US006410021B1

(12) United States Patent
Fuller et al.

(10) Patent No.: US 6,410,021 B1
(45) Date of Patent: Jun. 25, 2002

(54) VACCINES OF PASTEURELLACEAE MUTANTS AND VACCINATION METHOD

(76) Inventors: Troy E. Fuller, 2200 Lyons Ave., Lansing, MI (US) 48910; Martha H. Mulks, 1706 Germany Rd., Williamston, MI (US) 48895; Bradley Thacker, 903 Park Cir., Huxley, IA (US) 50124

( * ) Notice: Subject to any disclaimer, the term of this patent is extended or adjusted under 35 U.S.C. 154(b) by 0 days.

(21) Appl. No.: 09/064,935

(22) Filed: Apr. 22, 1998

Related U.S. Application Data

(62) Division of application No. 08/741,327, filed on Oct. 28, 1996, now Pat. No. 5,925,354.
(60) Provisional application No. 60/007,764, filed on Nov. 30, 1995.

(51) Int. Cl.⁷ ...................... A61K 39/00; A61K 39/102; A61K 45/00; A61K 39/12; C12N 1/36
(52) U.S. Cl. ............................... 424/184.1; 424/256.1; 424/825; 424/200.1; 424/235.1; 424/255.1; 424/282.1; 435/245; 935/65; 935/66; 935/72
(58) Field of Search ........................... 424/184.1, 256.1, 424/825, 200.1, 235.1, 255.1, 282.1; 435/245; 935/65, 66, 72

(56) References Cited

U.S. PATENT DOCUMENTS

| | | |
|---|---|---|
| 4,888,170 A | 12/1989 | Curtiss, III |
| 5,254,340 A | 10/1993 | Van Leengoed et al. |
| 5,332,572 A | 7/1994 | Ross et al. |
| 5,387,744 A | 2/1995 | Curtiss, III et al. |
| 5,389,386 A | 2/1995 | Winston et al. |
| 5,424,065 A | 6/1995 | Curtiss, III et al. |
| 5,429,818 A * | 7/1995 | Inzana |
| 5,456,914 A | 10/1995 | Stine et al. |
| 5,468,485 A | 11/1995 | Curtiss, III |
| 5,925,354 A * | 7/1999 | Fuller et al. |
| 5,925,538 A * | 7/1999 | Perkins et al. |
| 6,022,728 A * | 2/2000 | Mulks et al. |

FOREIGN PATENT DOCUMENTS

| | | |
|---|---|---|
| CA | 2045950 | 12/1992 |
| EP | 453024 | 10/1991 |
| EP | 595188 | 5/1994 |
| WO | WO 9409821 | 5/1994 |

OTHER PUBLICATIONS

Vilnis et al. Vet. Microbiol. 62/2:81–96, May 1998.*
Jollie et al. Vet. Microbiol. 45/4:383–391, 1995.*
Bandrin et al., Three linkage groups of genes involved in riboflavin biosynthesis in *Escherichia coli.*, Sov. Genet. 19: 1103–1109 (1983).
Bresler, S.E. et al., Genetika 9:84–91 (1973).
Inzana, T.J. et al., Infect. Immun. 61: 1682–1686 (1993).
Paltineanu, D.R. et al., Proc. Int. Pig. Vet. Soc. 12:214 (1992).
Perkins, J.B. et al., Biosynthesis of riboflavin, biotin, folic acid, and cobalamin, p. 319–334 (1993).
Perry, M.B. et al., Immunother. Infect. Dis. 4: 299–308 (1990).
Reeve, J., Molec. Gen. Genet. 158: 73–79 (1977).
Richter, G. et al., J. Bacteriol. 175: 4045–4051 (1993).
Thacker, B.J. et al., Proc. Int. Pig. Vet. Soc. 10: 87 (1988).
Utrera, V. et al., Proc. Int. Pig. Vet. Soc. 12: 213 (1988).
Doggett, T.A. et al., In J. E. Ciardi et al., Genetically Engineered Vaccines, Plenum Press, New York, pp. 165–173 (1992).
Tacket, C.O. et al., Infect. Immun. 60: 536–541 (1992).
Mulks, M.H. et al., Gene 165: 61–66 (1995).
Mulks, M.H. et al., J. Bacteriol. 177: 7265–7270 (1995).
West et al., Gene 160: 81–86 (1995).
Schott, J. Biol. Chem. 265: 4204–4209 (1990).
Fuller, T.E. et al, Infection and Immunity Nov. 1996 p. 4659–4664.
Fuller, T.E. et al, Vaccine 18 (2000) p. 2867–2877.

* cited by examiner

*Primary Examiner*—Nita Minnifield

(57) ABSTRACT

A live vaccine of recombinant mutants of a member of the family Pasteurellaceae lacking a rib gene necessary for production of riboflavin as well as a method of vaccination therewith is described. The vaccine is effective against members of the family Pasteurellaceae.

11 Claims, 12 Drawing Sheets

```
  1 AATTCGGTCGGACGTACTTT ATTTGAGCATATCAATGAAG GAGGTTTTGATTATGTGATT

-35
 61 TCAGAGTGTGAAACCTGTAA ATGGCAGATTGATATGTCGA GCAATGTGACTTGTTTACAT

-10
121 CCGATTACTTTATTATCAAT GGCATTGGATAAACGCTAAT TCTTGCTTGACTTTGACAAT

181 CAAAAGTCGCAAATTTGCAA CAATTTTTTAATAATCTTCA GGGCAGGGTGAAATTCCCGA

241 TCGGCGGTAAAGTCCGCGAG CCGAACGAAAAAGGTTTGGC AGGAACCGGTGAGATTCCGG

M  K  L  P   C  K  R  W  F  F  L
301 TACCGACAGTATAGTCTGGA TGGAAGAAGATGAAATTACC GTGTAAGCGGTGGTTTTCC

S  F  L  Q  A  L   R  S  K  D  F  K  A   F  F  I  I  R  V  N
361 TATCTTTTTTACAAGCCTTG AGATCGAAAGATTTCAAGGC TTTTTTCATCATTAGGGTAA

M  P  V  M  C  F   P  L  P  S  N  S  F   K  T  M  T  D  L  D
421 ACATGCCTGTAATGTGTTTT CCTCTGCCCTCAAATAGTTT CAAAACAATGACGGATTTAG

Y  M  R  R  A  I   A  L  A  K  Q  G  L   G  W  T  N  P  N  P
481 ACTATATGCGCCGTGCCATT GCACTGGCAAAACAAGGTTT AGGCTGGACGAATCCCAATC

L  V  G  C  V  I   V  K  N  G  E  I  V   A  E  G  Y  N  E  K
541 CGCTTGTCGGTTGTGTAATT GTCAAAAACGGTGAAATCGT TGCCGAAGGTTACCATGAAA

I  G  G  W  H  A   E  R  N  A  V  L  H   C  K  E  D  L  S  G
601 AGATTGGTGGATGGCATGCG GAACGTAATGCCGTTTTACA TTGTAAGGAAGATCTTTCCG

A  T  A  Y  V  T   L  E  P  C  C  H  H   G  R  T  P  P  C  S
661 GGGCGACTGCTTATGTAACG CTTGAGCCTTGTTGTCATCA CGGCCGCACGCCGCCTTGTT

D  L  L  I  E  R   G  I  K  K  V  F  I   G  S  S  D  P  N  P
721 CGGATTTATTAATTGAACGA GGCATTAAAAAAGTATTTAT CGGTTCGAGCGATCCGAATC

L  V  A  G  R  G   A  N  Q  L  R  Q  A   G  V  E  V  V  E  G
781 CTTTAGTAGCAGGGCGGGGA GCAAATCAGCTACGCCAAGC CGGCGTGGAAGTGGTGGAAG

L  L  K  E  E  C   D  A  L  N  P  I  F   F  H  Y  I  Q  T  K
841 GTTTACTCAAAGAAGAATGT GATGCGTTAAACCCGATTTT TTTCCACTATATTCAAACTA

R  P  Y  V  L  M   K  Y  A  M  T  A  D   G  K  I  A  T  G  S
901 AACGTCCGTATGTGCTAATG AAATATGCCATGACGGCAGA CGGCAAAATTGCAACCGGTA

G  E  S  K  W  I   T  G  E  S  A  R  A   R  V  Q  Q  T  R  H
961 GCGGCGAATCCAAATGGATT ACCGGTGAATCGGCAAGAGC AAGAGTGCAGCAAACACGTC

Q  Y  S  A  I  M   V  G  V  D  T  V  L   A  D  N  P  M  L  N
1021 ATCAATATAGTGCGATTATG GTCGGTGTAGATACGGTACT TGCCGATAACCCGATGTTAA
```

FIG. 4A

```
             S   R   M   P   N   A     K   Q   P   V   R   I   V     C   D   S   Q   L   R   T
        1081 ATAGCCGAATGCCGAATGCG     AAACAACCGGTCCGGATTGT     CTGCGATAGCCAATTACGTA

P   L   D   C   Q   L     V   Q   T   A   K   E   Y     R   T   V   I   A   T   V
        1141 CACCGTTAGATTGCCAGTTA     GTGCAGACAGCGAAAGAATA     TCGCACCGTAATTGCAACCG

S   D   D   L   Q   K     I   E   Q   F   R   P   L     G   V   D   V   L   V   C
        1201 TTAGTGACGATTTGCAAAAA     ATTGAACAATTTAGACCGCT     TGGCGTAGATGTATTAGTGT

K   A   R   N   K   R     V   D   L   Q   D   L   L     Q   K   L   G   E   M   Q
        1261 GTAAAGCACGAAACAAGCGG     GTAGATTTGCAAGATCTTTT     GCAAAAGCTCGGTGAAATGC

I   D   S   L   L   L     E   G   G   S   S   L   N     F   S   A   L   E   S   G
        1321 AGATCGACAGCCTCTTATTG     GAAGGCGGTTCAAGTTTGAA     TTTCAGTGCGTTAGAAAGCG

I   V   N   R   V   H     C   Y   I   A   P   K   L     V   G   G   K   Q   A   K
        1381 GTATCGTGAATCGAGTACAT     TGTTATATTGCGCCTAAATT     AGTCGGTGGTAAACAAGCGA

T   P   I   G   G   E     G   I   Q   Q   I   D   Q     A   V   K   L   K   L   K
        1441 AAACCCCAATCGGCGGTGAG     GGAATTCAACAAATCGACCA     AGCGGTTAAATTAAAATTGA

S   T   E   L   I   G     E   D   I   L   L   D   Y     V   V   I   S   P   L   *
        1501 AATCGACCGAACTCATCGGC     GAAGATATTTTGTTGGATTA     TGTAGTCATCTCCCCTCTTT

1561 AGCAAAGAGGGGTCGGGGGA     GATTTGAGATAATGTTGAAA     TTTACACCGCCTTTCACTTT

1621 GGCGTTGTTAAATCTCCCCT     AACCCCTCTTTACAAAAGAG     AGGGATCAATAATGAGGAAA

M   F   T   G   I   I     E   E   V   G   K   I     A   Q   I   H   K   Q   G
        1681 TTATATGTTCACAGGTATTA     TTGAAGAAGTCGGCAAAATT     GCTCAAATTCATAAGCAAGG

E   F   A   V   V   T   I     N   A   T   K   V   L     Q   D   V   H   L   G   D
        1741 CGAATTTGCGGTAGTCACAA     TTAATGCGACCAAAGTATTA     CAAGACGTTCATTTAGGCGA

T   I   A   V   N   G   V     C   L   T   V   T   S     F   S   S   N   Q   F   T
        1801 CACGATTGCGGTGAACGGCG     TATGTTTAACCGTAACTTCT     TTTTCGAGTAATCAGTTTAC

A   D   V   M   S   E   T     L   K   R   T   S   L     G   E   L   K   S   N   S
        1861 CGCCGATGTAATGTCGGAAA     CGTTAAAACGTACTTCATTA     GGCGAATTAAAGTCGAATAG

P   V   N   L   E   R   A     M   A   A   N   G   R     F   G   G   H   I   V   S
        1921 TCCGGTTAATTTAGAACGCG     CGATGGCGGCAAACGGACGT     TTCGGCGGACACATCGTTTC

G   H   I   D   G   T   G     E   I   A   E   I   T     P   A   H   N   S   T   W
        1981 GGGGCATATTGACGGCACCG     GCGAAATTGCGGAAATCACA     CCGGCACATAATTCGACATG

Y   R   I   K   T   S   P     K   L   M   R   Y   I     I   E   K   G   S   I   T
        2041 GTATCGCATTAAAACCTCTC     CAAAATTAATGCGTTATATT     ATTGAGAAAGGTTCGATCAC

I   D   G   I   S   L   T     V   V   D   T   D   D     E   S   F   R   V   S   I
        2101 CATTGACGGTATTAGCCTGA     CCGTAGTCGATACCGATGAT     GAAAGTTTCCGTGTATCGAT
```

FIG. 4B

```
              I  P  H  T  I  K  E      T  N  L  G  S  K         K  I  G  S  I  V  N
2161 TATTCCGCATACGATTAAAC   AAACCAATTTAGGTTCGAAA   AAAATCGGCAGTATTGTCAA

L  E  N  D  I  V  G      K  Y  I  E  Q  F         L  L  K  K  P  A  D
2221 TTTAGAAAATGATATTGTCG   GTAAATATATCGAACAGTTT   TTACTGAAAAAGCCGGCGGA

E  P  K  S  N  L  S      L  D  F  L  K  Q         A  G  F  *
2281 TGAGCCGAAAAGTAATCTTA   GTTTAGACTTTTAAAGCAG    GCGGGATTTTAAGATTTGTA

M  T  D
2341 GGACACACTGAGTGTATCCT   ACCGACAAAAATATATATTT   TAGGAAAAGAAGATGACAGA

F  Q  F  S  K  V  E         D  A  I  E  A  I            R  Q  G  K  I  I  L
2401 TTTCCAATTTTCAAAAGTAG   AAGATGCGATCGAAGCGATT   CGACAAGGCAAAATCATTTT

V  T  D  D  E  D  R         E  N  E  G  D  F            I  C  A  A  E  F  A
2461 AGTGACTGACGATGAAGATC   GCGAAAACGAAGGCGATTTT   ATCTGTGCGGCGGAATTTGC

T  P  E  N  I  N  F         M  A  T  Y  G  K            G  L  I  C  T  P  I
2521 CACACCGGAAAATATCAATT   TTATGGCAACTTACGGCAAA   GGTTTGATTTGTACGCCGAT

S  T  E  I  A  K  K         L  N  F  N  P  M            V  A  V  N  Q  D  N
2581 TTCAACCGAAATCGCTAAAA   AATTAAATTTCCATCCGATG   GTTGCGGTCAATCAAGATAA

H  E  T  A  F  T  V         S  V  D  H  I  D            T  G  T  G  I  S  A
2641 TCATGAAACGGCGTTTACCG   TATCGGTGGATCATATTGAT   ACGGGAACGGGTATCTCAGC

F  E  R  S  I  T  A         M  K  I  V  D  D            N  A  K  A  T  D  F
2701 TTTTGAGCGTTCGATTACCG   CAATGAAAATTGTCGATGAT   AATGCTAAAGCAACGGATTT

R  R  P  F  H  M  F         P  L  I  A  K  E            G  G  V  L  V  R  N
2761 CCGCCGCCCGGGGCATATGT   TTCCGTTAATCGCTAAAGAA   GGTGGAGTGTTAGTGCGTAA

G  H  T  E  A  T  V         D  L  A  R  L  A            G  L  K  H  A  G  L
2821 CGGTCATACCGAAGCAACAG   TGGATTTAGCTCGTTTAGCC   GGTTTAAAACACGCCGGTTT

C  C  E  I  M  A  D         D  G  T  M  M  T            M  P  D  L  Q  K  F
2881 ATGTTGTGAAATTATGGCGG   ATGACGGCACGATGATGACT   ATGCCGGATCTACAAAAATT

A  V  E  H  N  M  P         F  I  T  I  Q  Q            L  Q  E  Y  R  R  K
2941 TGCGGTAGAACACAATATGC   CGTTTATCACGATTCAACAA   TTACAAGAATATCGCCGTAA

N  D  S  L  V  K  Q         I  S  V  V  K  M            P  T  K  Y  G  E  F
3001 GCATGACAGCTTGGTGAAAC   AAATTTCTGTGGTAAAAATG   CCGACAAAATACGGTGAGTT

M  A  H  S  F  V  E         V  I  S  G  K  E            H  V  A  L  V  K  G
3061 TATGGCACATAGCTTTGTTG   AAGTGATTTCAGGTAAAGAA   CACGTTGCGTTAGTCAAAGG

D  L  T  D  G  E  Q         V  L  A  R  I  H            S  E  C  L  T  G  D
3121 CGATTTAACCGACGGTGAGC   AAGTATTGGCGCGTATCCAT   TCGGAATGTTTAACCGGTGA

A  F  G  S  Q  R  C         D  C  G  Q  Q  F            A  A  A  M  T  Q  I
3181 CGCTTTCGGTTCTCAACGTT   GTGATTGCGGTCAGCAATTT   GCCGCAGCAATGACCCAAAT
```

FIG. 4C

```
              E  Q  E  G  R  G  V      I  L  Y  L  R  Q      E  G  R  G  I  G  L
3241   TGAGCAAGAGGGCAGAGGTG   TGATTCTGTATTTACGCCAA   GAAGGTCGTGGTATCGGTTT

I  N  K  L  R  A  Y      E  L  Q  D  K  G      M  D  T  V  E  A  N
3301   AATCAATAAGCTACGTGCTT   ACGAACTACAAGATAAAGGG   ATGGATACCGTTGAAGCGAA

V  A  L  G  F  K  E      D  S  R  E  Y  Y      I  G  A  Q  M  F  Q
3361   CGTCGCTTTAGGATTTAAAG   AAGACGAACGTGAGTACTAT   ATCGGTGCACAAATGTTCCA

Q  L  G  V  K  S  I      R  L  L  T  N  N      P  A  K  I  E  G  L
3421   GCAGTTAGGCGTAAAATCGA   TCCGTTTATTAACCAATAAT   CCGGCAAAAATTGAAGGCTT

K  E  Q  G  L  N  I      V  A  R  E  P  I      I  V  E  P  N  K  N
3481   AAAAGAGCAAGGATTAAATA   TCGTTGCACGTGAGCCGATT   ATTGTAGAACCGAACAAAAA

D  I  D  Y  L  K  V      K  Q  I  K  M  G      N  M  F  N  F  *
3541   TGACATTGATTACCTAAAAG   TCAAACAGATAAAAATGGGG   CATATGTTTAACTTCTAACT

-35
3601   TTAACAACCGTATGTAGTAT   TAGGGAAGCAAGCGTTGCGT   CCCTACTATAGAATGATACA

-10                                       M  A  K  I
3661   AGCGGTCACTTTTTTATAAA   ATTTGCATATTTCGAGAGG   ACAAAAAAATGGCAAAGATT

T  G  N  L  V  A  T      G  L  K  F  G  I  V      T  A  R  F  N  D
3721   ACAGGTAACTTAGTTGCGAC   AGGTTTAAAATTCGGTATTG   TAACCGCACGTTTCAACGAT

F  I  N  D  K  L  L      S  G  A  I  D  T  L      V  R  H  G  A  Y
3781   TTTATCAACGATAAATTATT   AAGCGGTGCAATTGATACGT   TAGTGCGTCACGGTGCGTAT

E  N  D  I  D  T  A      W  V  P  G  A  F  E      I  P  L  V  A  K
3841   GAAAACGATATTGATACGGC   ATGGGTTCCGGGTGCATTTG   AGATTCCATTAGTTGCGAAA

K  M  A  N  S  G  K      Y  D  A  V  I  C  L      G  T  V  I  R  G
3901   AAAATGGCAAACAGCGGTAA   ATATGATGCGGTAATCTGTT   TAGGTACGGTAATTCGCGGT

S  T  T  H  Y  D  Y      V  C  N  E  A  A  K      G  I  G  A  V  A
3961   TCGACAACTCACTATGATTA   CGTATGTAATGAAGCGGCAA   AAGGTATCGGTGCGGTAGCA

L  E  T  G  V  P  V      I  F  G  V  L  T  T      E  N  I  E  Q  A
4021   TTAGAAACCGGCGTACCGGT   AATTTTCGGTGTATTAACCA   CAGAAAATATTGAACAGGCG

I  E  R  A  G  T  K      A  G  N  K  G  S  E      C  A  L  G  A  I
4081   ATTGAACGCGCGGGTACTAA   AGCAGGTAATAAAGGTTCAG   AATGTGCATTAGGCGCAATC

E  I  V  N  V  L  K      A  I  *
4141   GAAATAGTAAACGTATTAAA   AGCGATCTAATTTTCGTTTG   ACGTGCTAAAAACAAGCGGT

4201   CGTTTTTGACTGGAATTTTG   CAAATTTCCCGTTAAAAACG   ACCGCTTATATTTTATGTCT

4253   AGTAAAGACCTTCTTTCTCG   TACCAGATTTTGTTGATATA   TAGCAAGCTTGG    4312
```

FIG. 4D

VACCINES OF PASTEURELLACEAE MUTANTS AND VACCINATION METHOD

CROSS REFERENCE TO RELATED CASES

This application is a divisional of application Ser. No. 08/741,327, filed on Oct. 28, 1996 now U.S. Pat. No. 5,925,354, which includes the disclosure in provisional patent application serial No. 60/007,764 filed Nov. 30, 1995, for Characterization of *Actinobacillus pleuropneumoniae* Riboflavin Biosynthesis Genes, hereby incorporated by reference.

TECHNICAL FIELD

The invention relates to vaccines and in particular, live vaccines against *Actinobacillus pleuropneumoniae* (APP) and related bacterial pathogens. The invention is also concerned with recombinant techniques for preparing such a vaccine.

BACKGROUND OF THE INVENTION

An organism known as *Actinobacillus pleuropneumoniae* (APP) is a gram negative coccobacillus organism that is found in the pig and causes pneumonia in the pig.

This disease is characteristically an acute necrotizing hemorrhagic bronchopneumonia, with accompanying fibrinous pleuritis (Fenwick, B. and S. Henry. 1994. Porcine pleuropneumonia. J. Am. Vet. Med. Assoc. 204:1334–1340) (Sebunya, T. N. K. and J. R. Saunders. 1983. *Haemophilus pleuropneumoniae* infection in swine: a review. J. Am. Vet. Med. Assoc. 182:1331–1337). Porcine pleuropneumonia is an economically devastating, severe and often fatal disease with clinical courses ranging from hyperacute to chronic infection (Fenwick, B. and S. Henry. 1994. Porcine pleuropneumonia. J. Am. Vet. Med. Assoc. 204:1334–1340) (Hunneman, W. A. 1986. Incidence, economic effects, and control of *Haemophilus pleuropneumoniae* infections in pigs. Vet. Quarterly 8:83–87). The existence of at least twelve antigenically distinct capsular serotypes (Perry, M. B., E. Altman, J.-R. Brisson, L. M. Beynon, and J. C. Richards. 1990. Structural characteristics of the antigenic capsular polysaccharides and lipopolysaccharides involved in the serological classification of *Actinobacillus pleuropneumoniae* strains. Serodiag. Immunother. Infect. Dis. 4:299–308) has made development of a cross-protective vaccine difficult. Killed whole cell bacterins provide at best serotype-specific protection (Nielsen, R. 1984. *Haemophilus pleuropneumoniae* serotypes—Cross protection experiments. Nord. Vet. Med. 36:221–234) (Nielsen, R. 1976. Pleuropneumonia of swine caused by *Haemophilus pleuropneumoniae*. Studies on the protection obtained by vaccination. Nord. Vet. Med. 28:337–338) (Rosendal, S., D. S. Carpenter, W. R. Mitchell, and M. R. Wilson. 1981. Vaccination against pleuropneumonia in pigs caused by *Haemophilus pleuropneumoniae*. Can. Vet. J. 22:34–35) (Thacker, B. J., and M. H. Mulks. 1988. Evaluation of commercial *Haemophilus pleuropneumoniae* vaccines. Proc. Int. Pig Vet. Soc. 10:87). In contrast, natural or experimental infection with a highly virulent serotype of *A. pleuropneumoniae* elicits protection against reinfection with any serotype (Nielsen, R. 1979. *Haemophilus parahaemolyticus* serotypes: pathogenicity and cross immunity. Nord. Vet. Med. 31:407–413) (Nielsen, R. 1984. *Haemophilus pleuropneumoniae* serotypes—Cross protection experiments. Nord. Vet. Med. 36:221–234) (Nielsen, R. 1974. Serological and immunological studies of pleuropneumonia of swine caused by *Haemophilus parahaemolyticus*. Acta Vet. Scand. 15:80–89). In several recent studies, attenuated strains of *A. pleuropneumoniae* produced by chemical nutagenesis, serial passage, or other undefined spontaneous mutation have been tested as live vaccines, with promising results (Inzana, T. J., J. Todd, and H. P. Veit. 1993. Safety, stability and efficacy of nonencapsulated mutants of *Actinobacillus pleuropneumoniae* for use in live vaccines. Infect. Immun. 61:1682–1686) (Paltineanu, D., R. Pambucol, E. Tirziu, and I. Scobercea. 1992. Swine infectious pleuropneumonia: Aerosol vaccination with a live attenuated vaccine. Proc. Int. Pig. Vet. Soc. 12:214) (Utrera, V., C. Pijoan, and T. Molitor. 1992. Evaluation of the immunity induced in pigs after infection with a low virulence strain of *A. pleuropneumoniae* serotype 1. Proc. Int. Pig. Vet. Soc. 12:213). However, the use of live vaccines in the field is problematic, particularly when the attenuating lesion in the vaccine strain has not been genetically defined. A well-defined mutation that prevents reversion to wild-type would be extremely desirable for the development of a live attenuated vaccine against *Actinobacillus pleuropneumoniae*.

A variety of mutations in biosynthetic pathways are known to be attenuating in other organisms. Lesions in aro(Hoiseth S. K. and B. A. D. Stocker. 1981. Aromatic-dependent *Salmonella typhimurium* are non-virulent and effective as live vaccines. Nature (london). 291: 238–239) (Homchampa, P., R. A. Strugnell and B. Adler. 1992. Molecular analysis of the aroA gene of *Pasteurella multocida* and vaccine potential of a constructed aroA mutant. Mol. Microbiol. 6: 3585–3593) (Homchampa, P., R. A. Strugnell and B. Adler. 1994. Construction and vaccine potential of an aroA mutant of *Pasteurella haemolytica*. Vet. Microbiol. 42:35–44) (Karnell, A., P. D. Cam, N. Verma and A. A. Lindberg. 1993. AroD deleteion attenuates *Shigella flexneri* strain 2457T and makes it a safe and efficacious oral vaccine in monkeys. Vaccine 8:830–836.) (Lindberg, A. A., A. Karnell, B. A. D. Stocker, S. Katakura, H. Sweiha and F. P. Reinholt. 1988. Development of an auxotrophic oral live *Shigella flexneri* vaccine. Vaccine 6:146–150) (O'Callaghan, D. D. Maskell, F. Y. Lieu, C. S. F. Easmon and G. Dougan. 1988. Characterization of aromatic and purine dependent *Salmonella typhimurium:* attenuation, persistence and ability to induce protective immunity in BALB/c mice. Infect. Immun. 56:419–423) (Vaughan, L. M., P. R. Smith, and T. J. Foster. 1993. An aromatic-dependent mutant of the fish pathogen *Aeromonas salmonicida* is attenuated in fish and is effective as a live vaccine against the Salmonid disease furunculosis. Infect. Immun. 61:2172–2181), pur (O'Callaghan, D. D. Maskell, F. Y. Lieu, C. S. F. Easmon and G. Dougan. 1988. Characterization of aromatic and purine dependent *Salmonella typhimurium:* attenuation, persistence and ability to induce protective immunity in BALB/c mice. Infect. Immun. 56:419–423) (Sigwart, D. F., B. A. D. Stocker, and J. D. Clements. 1989. Effect of a purA mutation on the efficacy of Salmonella live vaccine vectors. Infect. Immun. 57:1858–1861), and thy (Ahmed, Z. U., M. R. Sarker, and D. A. Sack. 1990. Protection of adult rabbits and monkeys from lethal shigellosis by oral immunization with a thymine-requiring and temperature-sensitive mutant of *Shigella flexneri* Y. Vaccine. 8:153–158) loci, which affect the biosynthesis of aromatic amino acids, purines, and thymine, respectively, are attenuating because they eliminate the ability of the bacterium to synthesize critical compounds that are not readily available within mammalian hosts. For example, aro mutants of Salmonella and Shigella species have been shown to be attenuated in their natural hosts (Hoiseth S. K. and B. A. D. Stocker. 1981. Aromatic-dependent *Salmonella typhimu-*

*rium* are non-virulent and effective as live vaccines. Nature (london). 291: 238–239) (Homchampa, P., R. A. Strugnell and B. Adler. 1992. Molecular analysis of the aroA gene of *Pasteurella multocida* and vaccine potential of a constructed aroA mutant. Mol. Microbiol. 6: 3585–3593) (Homchampa, P., R. A. Strugnell and B. Adler. 1994. Construction and vaccine potential of an aroA mutant of *Pasteurella haemolytica*. Vet. Microbiol. 42:35–44) (Karnell, A., P. D. Cam, N. Verma and A. A. Lindberg. 1993. AroD deletion attenuates *Shigella flexneri* strain 2457T and makes it a safe and efficacious oral vaccine in monkeys. Vaccine 8:830–836) (Lindberg, A. A., A. Karnell, B. A. D. Stocker, S. Katakura, H. Sweiha and F. P. Reinholt. 1988. Development of an auxotrophic oral live *Shigella flexneri* vaccine. Vaccine 6:146–150) (O'Callaghan, D. D. Maskell, F. Y. Lieu, C. S. F. Easmon and G. Dougan. 1988. Characterization of aromatic and purine dependent *Salmonella typhimurium*: attenuation, persistence and ability to induce protective immunity in BALB/c mice. Infect. Immun. 56:419–423). Lesions that affect the biosynthesis of LPS (Collins, L. V., S. Attridge, and J. Hackett. 1991. Mutations at rfc or pmi attenuate *Salmonella typhimurium* virulence for mice. Infect. Immun. 59:1079–1085) (Nnalue, N. A., and B. A. D. Stocker. 1987. Tests of the virulence and live-vaccine efficacy of auxotrophic and gale derivatives of *Salmonella cholerasuis*. Infect. Immun. 55:955–962) and of cyclic AMP (Kelly, S. M., B. A. Bosecker and R. Curtiss III. 1992. Characterization and protective properties of attenuated mutants of *Salmonella cholerasuis*. Infect. Immun. 60:4881–4890) (Tacket, C. I., D. M. Hone, R. Curtiss III, S. M. Kelly, G. Losonsky, L. Guers. A. M. Harris, R. Edelman. M. M. Levine. 1992. Comparison of the safety and immunogenicity of ΔaroC ΔaroD and ΔcyaΔcrp *Salmonella typhi* strains in adult volunteers. Infect. Immun. 60:536–541) have also been shown to be attenuating in Salmonella species. It is important to note that not all attenuating mutations are good vaccine candidates in different organisms because some attenuating mutations result in poor persistence and immunogenicity (O'Callaghan, D. D. Maskell, F. Y. Lieu, C. S. F. Easmon and G. Dougan. 1988. Characterization of aromatic and purine dependent *Salmonella typhimurium*: attenuation, persistence and ability to induce protective immunity in BALB/c mice. Infect. Immun. 56:419–423) (Sigwart, D. F., B. A. D. Stocker, and J. D. Clements. 1989. Effect of a purA mutation on the efficacy of Salmonella live vaccine vectors. Infect. Immun. 57:1858–1861).

Riboflavin (vitamin B2), a precursor of the coenzymes flavin adenine dinucleotide (FAD) and flavin mononucleotide (FMN), is essential for basic metabolism. It is synthesized by plants and by most microorganisms but not by higher animals (Bacher, A. 1991. Biosynthesis of flavins. p. 215–59. In F. Muller (ed.), Chemistry and Biochemistry of Flavins, Vol. 1. Chemical Rubber Company, Boca Raton, Fla.). Many pathogenic bacteria are apparently unable to utilize flavins from their environment and are entirely dependent on endogenous production of riboflavin (Schott, K., J. Kellerman, F. Lottspeich and A. Bacher. 1990. Riboflavin syntheses of *Bacillus subtilis*: purification and amino acid sequence of the α-subunit. J. Biol.Chem. 265:4204–4209). Even with the ability to utilize exogenous riboflavin, there may not be enough of the vitamin present in mammalian host tissues to permit growth, particularly not in sites devoid of normal bacterial flora.

Vaccines are preparations used to prevent specific diseases in animals by inducing immunity. This is accomplished by exposing a patient to an antigen from an agent capable of causing a particular disease which, in turn, causes the immune system of the patient to produce large Quantities of antibody. The presence of the antibody in the patient's blood protects the patient from a later attack by the disease-causing agent. Vaccines may either be composed of subunits of the agent, or the live or killed agent itself. If a live vaccine is to be used, its virulence must be attenuated in some way; otherwise, the vaccine will cause the disease it is intended to protect against. See U.S. Pat. No. 5,429,818, Col. 1.

Most current vaccines against APP are killed whole cell bacterins, that is, whole bacterial cells killed by heat treatment or formalinization, suspended in an adjuvant solution. Some alternative ways of attempting to develop vaccines against APP are the use of subunit vaccines and the use of non-encapsulated mutants.

The use of a protease lysate of the outer membrane of *A. pleuropneumoniae* cells as a vaccine against APP infection is described in U.S. Pat. No. 5,332,572.

The use of extracellular proteins and/or hemolysins from APP as vaccines against APP infection is described in U.S. Pat. No. 5,254,340, WO Patent No. 9409821, EP No. 595,188, CA 2045950, and EP No. 453,024.

The use of non-encapsulated mutants of APP is described in U.S. Pat. No. 5,429,818. It disclosed that the capsule of such bacteria is required for virulence. Therefore, the preparation of a mutant of APP that was a non-capsulated mutant was described as a vaccine.

A method of administering vaccines to pigs by a transthoracic intrapulmonary immunization is described in U.S. Pat. No. 5,456,914.

A vaccine for the immunization of an individual against *Salmonella choleraesuis* utilizing derivatives that are incapable of producing functional adenylate cyclase and/or cyclic AMP receptor protein is described in U.S. Pat. No. 5,468,485. The avirulent *S. choleraesuis* was made avirulent by an inactivating mutation in a cya gene and an inactivating mutation in a crp gene. Similar techniques are described in other bacteria in U.S. Pat. Nos. 5,424,065; 5,389,386; 5,387,744 and 4,888,170.

To protect animals from lung disease, it is needed to achieve a sufficiently high level of antibodies, particularly IgA antibodies, in the lungs to prevent adherence of invading microorganisms to mucosal surfaces and neutralize potentially damaging virulence factors. Antibodies in the patient's serum or at the mucosal surfaces can be important to protection. One of the reasons for using a live vaccine instead of a killed whole cell bacterin is that a live vaccine, given intranasally or orally, can induce specific local secretory antibody in the secretions that cover mucosal surfaces. This local antibody is often quite helpful for protection against diseases that infect at or through mucosal surfaces.

None of the patents pertain to a recombinant technique for a relatively convenient method for obtaining genetically defined mutants for use in a vaccine against APP.

It is believed that a mutation in a critical biosynthetic pathway which limits growth in vivo but does not otherwise alter expression of important antigens such as capsular polysaccharide, lipopolysaccharide and extracellular toxins, could produce an attenuated vaccine strain capable of inducing cross-protective immunity against *A. pleuropneumoniae*.

It is believed that riboflavin biosynthesis would be essential for survival of *A. pleuropneumoniae* in vivo, and that mutations in the riboflavin biosynthetic pathway would be attenuating due to the scarcity of riboflavin present on the mucosal surfaces of the respiratory tract.

It is an object of the present invention to describe the use of mutations in the riboflavin biosynthetic pathway to construct attenuated strains of pathogenic bacteria for use as live vaccines, with a riboflavin-requiring mutant of APP used as a specific example.

It is an object of the present invention to describe a live vaccine against APP utilizing a riboflavin mutation in the APP genome.

SUMMARY OF THE INVENTION

Described is a live vaccine against bacterial pathogens comprising a recombinant riboflavin-requiring mutant having a mutation that inactivates riboflavin biosynthesis therein. In particular, this includes bacterial pathogens in the family Pasteurellaceae, which include animal pathogens as *Actinobacillus pleuropneumoniae, Actinobacillus suis, Haemophilus parasuis, Pasteurella haemolytica* and *Pasteurella multocida*, as well as human pathogens *Haemophilus influenzae* and *Haemophilus ducreyi*.

Also described is a live vaccine against *Actinobacillus pleuropneumoniae* (APP) comprising a recombinant APP having an attenuating inactivating mutation therein.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 4A to 4D show shows the complete nucleotide sequence of APP ribGBAH operon and flanking regions and the predicted amino acid sequences of the encoded proteins.

DESCRIPTION OF PREFERRED EMBODIMENTS

Figure 1:
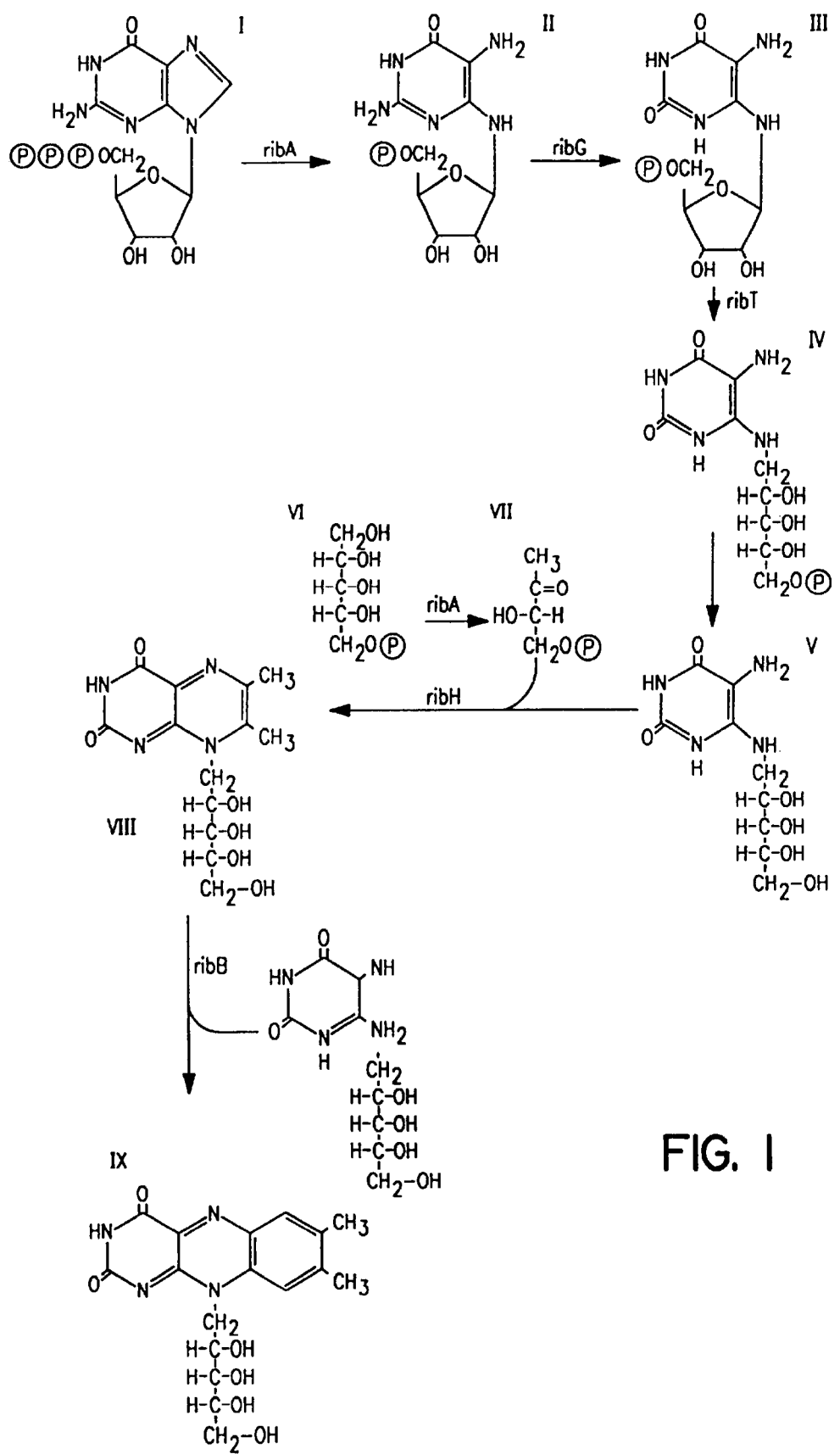
FIG. 1 describes a proposed a metabolic pathway for bacterial riboflavin synthesis.

The present application pertains to the development of attenuated mutants of the pathogenic bacterium *A. pleuropneumoniae* which contain mutations in the genome, specifically in the genes encoding the enzymes involved in the biosynthesis of riboflavin. By "mutation" is meant not just a random selection of variations of the genome of APP but utilization of well known recombinant techniques for specifically modifying the genome of APP. Accordingly, therefore, it is desirable to ascertain the riboflavin biosynthesis genes of APP.

By "attenuated" is meant a reduction in the severity, virulence or vitality of the disease causing agent.

After determining the sequence and organization of the riboflavin genes, one is then able to modify APP by removing some or all of such genes, thereby attenuating the pathogen, i.e., making the pathogen avirulent.

After a strain of avirulent APP is obtained, it could then be utilized as a live vaccine. Described below are the detailed steps broadly outlined above.

Identifying, Cloning, and Sequencing of the Riboflavin Biosynthesis Genes from APP Cloning of riboflavin genes from APP is described in the paper entitled "Characterization of APP Riboflavin Biosynthesis Genes", Journal of Bacteriology, December, 1995, pages 7265–7270 by Fuller and Mulks. This is incorporated herein by reference.

*Actinobacillus pleuropneumoniae* (APP) is the causative agent of porcine pleuropneumonia (9,23,39). The disease is characteristically an acute necrotizing hemorrhagic bronchopneumonia, with accompanying fibrinous pleuritis (9,39). Pleuropneumonia is an economically devastating, severe and often fatal disease with clinical courses ranging from peracute to chronic infection (9,14). The existence of at least twelve antigenically distinct capsular serotypes (31) has made development of a cross-protective vaccine difficult. Killed whole cell bacterins provide at best serotype-specific protection (25,26,35,43). In contrast, natural or experimental infection with virulent APP frequently elicits protection against reinfection with any serotype (24,25,27). Avirulent strains of APP have been tested as live vaccines and have elicited cross-protective immunity against subsequent challenge (15,28,44). However, the use of live vaccines in the field is problematic, particularly when the attenuating lesions in the vaccine strain have not been genetically defined. Development of attenuated strains with defined biochemical mutations that limit growth in vivo and prevent reversion to wild type is a promising approach to improved vaccines against APP infection.

Riboflavin (vitamin B2), a precursor of the coenzymes flavin adenine dinucleotide (FAD) and flavin mononucleotide (FMN), is essential for basic metabolism. It is synthesized by plants and by most microorganisms but not by higher animals (1). Many pathogenic bacteria are apparently unable to utilize flavins from their environment and are entirely dependent on endogenous production of riboflavin (38). Therefore, riboflavin biosynthesis may be essential for survival of pathogens in vivo, and mutations in the riboflavin biosynthetic pathway nay be attenuating.

The proposed metabolic pathway for bacterial riboflavin synthesis shown in FIG. 1 begins with guanosine triphosphate (GTP) as the precursor (for a review see reference 1). The most extensively studied system for bacterial riboflavin synthesis is *Bacillus subtilis* (for a review see reference 29). The *B. subtilis* riboflavin synthesis genes are located and coregulated in an operon structure (12) that consists of five open reading frames designated as ribG, rib B, rib A, ribH and ribT (19,29). The ribGBAHT genes encode, respectively, a rib-specific deaminase; the α-subunit of riboflavin synthase (lumazine synthase) a bifunctional enzyme containing GTP cyclohydrase and 3,4-dihydroxy 2-butanone 4-phosphate synthase (DHBP) activities; the β-subunit of riboflavin synthase; and a rib-specific reductase (29). The complete sequence of the *B. subtilis* riboflavin operon has been determined in two individual laboratories (19,30). The *B. subtilis* structural ribGBAHT genes code for predicted proteins of 361 (MW 39,700), 215 (MW 23,600), 398 (MW 43,800), 154 (MW 16,900), and 124 (MW 13,600) amino acids in length (19, 29). Two functional promoters have been identified in the *B. subtilis* rib operon. The main promoter, P1, for which a transcriptional start site has been determined 294 base pairs (bps) upstream of ribG (12,30), is responsible for transcription of all five structural genes (12). Another promoter, P2, produces a secondary transcript encoding the last three genes of the operon, ribAHT (12). A possible third promoter has been postulated that would express ribH (7). In addition, the operon has been shown to be transcriptionally coregulated (30) by a transacting repressor, RibC (3,6), which acts at a regulatory site, ribO (3,20), upstream of ribG, apparently by a transcription termination-antitermination mechanism (29). The RibC repressor appears to respond to FMN and FAD, as well as to riboflavin and several of its biosynthetic intermediates, and regulates expression from both ribP1 and ribP2 (4,20,29).

*E. coli* is the second most chemically characterized system for riboflavin synthesis. In contrast to *B. subtilis*, the rib genes of *E. coli* are scattered around the chromosome and are expressed constituitively (2,46). Rather than having a bifunctional ribA, *E. coli* has two separate genes, ribB and ribA, that encode the functions of 3,4-DHBP synthase (34) and GTP cyclohydrase II (33), respectively. ribB is homologous to the 5' end of *B. subtilis* ribA while ribA is homologous to the 3' end (33,34). *E. coli* genes with sequence homology to the *B. subtilis*; ribG (42), ribH (42), and ribB genes have also been identified.

Identified herein is a fragment of APP serotype 5 chromosomal DNA that triggers overproduction of riboflavin when cloned in *E. coli*. Nucleotide sequence analysis demonstrated four open reading frames with significant identity and a similar operon arrangement to the ribGBAH genes from *Bacillus subtilis*.

Materials and Methods

Bacterial strains and media. *A. pleuropneumoniae* ISU178, a serotype 5 strain, was cultured at 37° C. in brain heart infusion broth or agar (Difco Laboratories, Detroit, Mich.) containing 10 μg/ml nicotinamide adenine dinucleotide (NAD) (Sigma Chemical Company, St. Louis, Mo.). *E. coli* DH5-α (supE44), ΔlacU169, (φ80lacZΔM15), hsdR17, recA1, endA1, gyrA96, thi-1, relA1) was used for construction of the APP genomic library. *E. coli* strain DS410 (azi-8, tonA2, minA1, minB2, rpsL135, xyl-7, mtl-2, thi-1, λ-) was used for minicell isolation and protein labeling experiments. *E. coli* ribA:Tn5 (BSV18), ribB:Tn5 (BSV11) and ribC:Tn5 (BSV3) mutants used for complementation studies were described by Bandrin et al (2) and are available from Barbara Bachmann (*E. coli* Genetic Stock Center, Yale University). *E. coli* strains were cultured in Luria-Bertani medium or in M9 (36) supplemented with 15 g/L NZ (amine (Sigma) and with riboflavin at 200 μg/mL when necessary. Ampicillin was added to 100 μg/ml for plasmid selection.

DNA manipulations. DNA modifying enzymes were supplied by Boehringer-Mannheim Biochemicals (Indianapolis, Ind.) and used according Lo manufacturer's specifications. Genomic and plasmid DNA preparations, gel electrophoresis, and *E. coli* transformation were all performed by conventional methods (36).

Cloning and sequencing. APP serotype 5 genomic DNA was digested with HindIII and fragments ranging in size from 4 to 7 kb were ligated into the HindIII site in the polylinker of the plasmid vector pUC19 (45). A recombinant plasmid, designated pTF10, which overproduced riboflavin was isolated from this library. Unidirectional nested deletions were constructed with exonuclease III and S1 nuclease digestion, using the Erase-a base system (Promega Corp., Madison, Wis.). Nucleotide sequencing was performed on alkali-denatured double-stranded DNA by the dideoxy chain-termination method of Sanger et al. (37) using the Sequenase 2.0 kit (U.S. Biochemical, Cleveland, Ohio) and [$^{35}$S]dATP (adenosine triphosphate) (Amersham Corp., Arlington Heights, Ill.). Sequencing primers used included universal forward and reverse primers for pUC sequencing (U.S. Biochemicals), as well as several oligonucleotide primers designed from previously obtained sequence data. These internal primers were synthesized by the Michigan State University Macromolecular Structure Facility and included MM4 (5'-AAT-CCG-GCA-AAA-ATT-GAA-GGC-3') (Sequence ID No:1), MM5 (5'-GCA-CCG-TGA-CGC-ACT-AAC-G-3') (Sequence ID No: 2), MM6 (5'-GCG-CCA-ATA-CTT-GCT-CAC-CG-3') (Sequence ID No: 3), MM9 (5'-GGT-TTC-TTT-ATT-CGT-ATG-CGG-3') (Sequence ID No: 4), MM10 (5'-TCA-AGA-AGT-CGG-CAA-ATT-GCT-C-3') (Sequence ID No: 5), MM11 (5'-CGG-ATT-GGG-ATT-CGT-CCA-GCC-3') (Sequence ID No: 6), MM13 (5'-GGC-C-AC-ACG-ATT-GCG-GTG-3') (Sequence ID No: 7), MM14 (5'-GCC-AGT-TAG-TGC-AGA- CAG-CG-3') (Sequence ID No: 8), and MM38 (5'-CTC-ACC-GGT-TCC-TGC-CAA-ACC-3') (Sequence ID No: 9).

DNA sequences were analyzed using the GCG sequence analysis programs (11).

Mass spectroscopy. Positive and Negative Ion Fast Atom Bombardment (FAB) mass spectroscopy was performed at the Michigan State University Mass Spectroscopy Facility.

Quantification of riboflavin. Bacterial cells were pelleted in a microcentrifuge, and the absorbance at 445 nm of the culture supernatant was measured using a Beckman DU-7 spectrophotometer (Beckman Instruments, Fullerton, Calif.). The absorbance at 445 nm was multiplied by a factor of 31.3 to yield the riboflavin concentration in mg/liter (10).

Minicell Analysis. The minicell-producing *E. coli* strain DS410 (32) was transformed by calcium chloride/heat shock treatment with pUC19 or pTF rib clones. Transformant colonies which produced a large number of minicells were selected by microscopy. Cultures were grown overnight at 37° C. in 500 mL LB broth, and minicells were isolated by differential centrifugation followed by glass fiber filtration as described by Christen et al (8). Minicells were resuspended to an $OD_{590}$ of 0.5–1.0 in 200 μl labeling mix (22.0 ml M9 media, 20.0 ml 50 mM HEPES (N-[2-hydroxyethyl] piperazine)-N'-2 ethanesulfonic acid) pH 7.5, 2.5 ml of 20% glucose, 0.05 ml of 10 mg/ml adenine, 0.05 ml of 10 mg/ml pyridoxine, 5.0 ml of NEDA amino acid stock (21) lacking methionine and cysteine, and 0.2 ml of 10 mg/ml cycloserine-D) and incubated at 37° C. for 30 minutes. Trans-label ([$^{35}$S]methionine plus [$^{35}$S]cysteine, ICN Biomedicals, Irvine, Calif.) was added to a final concentration of 22 μCi per reaction and cells were incubated at 37° C. for 1 hour. Total and TCA (trichloroacetic acid) precipitable counts were measured by liquid scintillation counting to determine amount of incorporation. Cells were pelleted in a microcentrifuge and washed with cold HEPES (50 mM,pH7.5) plus 10 mM methionine plus 10 mM cysteine. Labeled proteins (50,000 cpm/lane) were separated by discontinuous SDS-PAGE on a 12% polyacrylamide gel and were visualized by autoradiography on Kodak XAR-5 film.

Nucleotide sequence accession number. The nucleotide sequence of the *A. pleuropneumoniae* ribGBAH genes has been submitted to GenBank and assigned an accession number of: U27202.

Results

Figure 2:
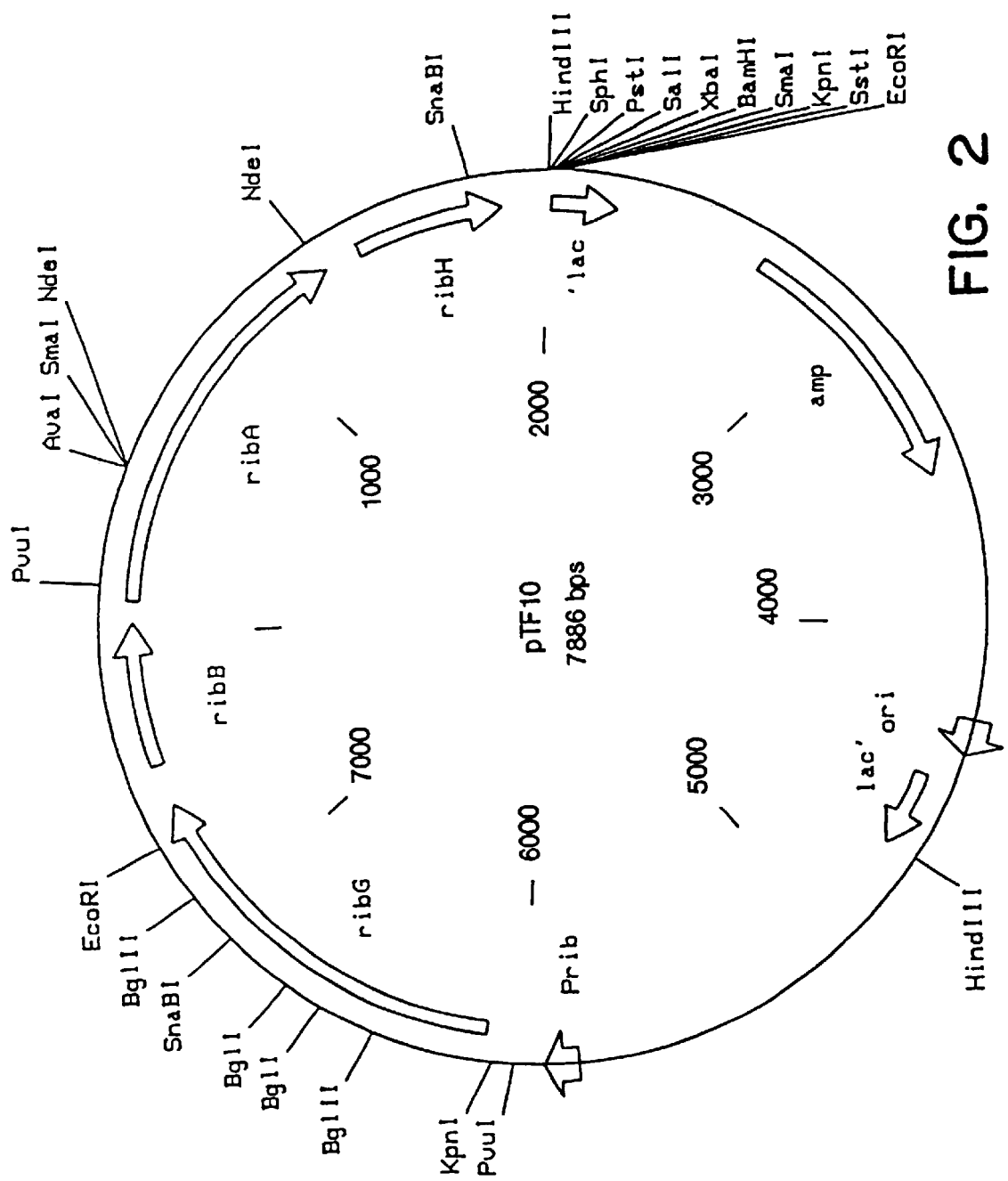
FIG. 2 is a physical map of a plasmid contruct pTF-10, which comprises a 5.2 Kb fragment of *A. pleuropneumoniae* chromosomal DNA, including the APP riboflavin biosynthetic operon, cloned into the vector pUC19.
Figure 3A:
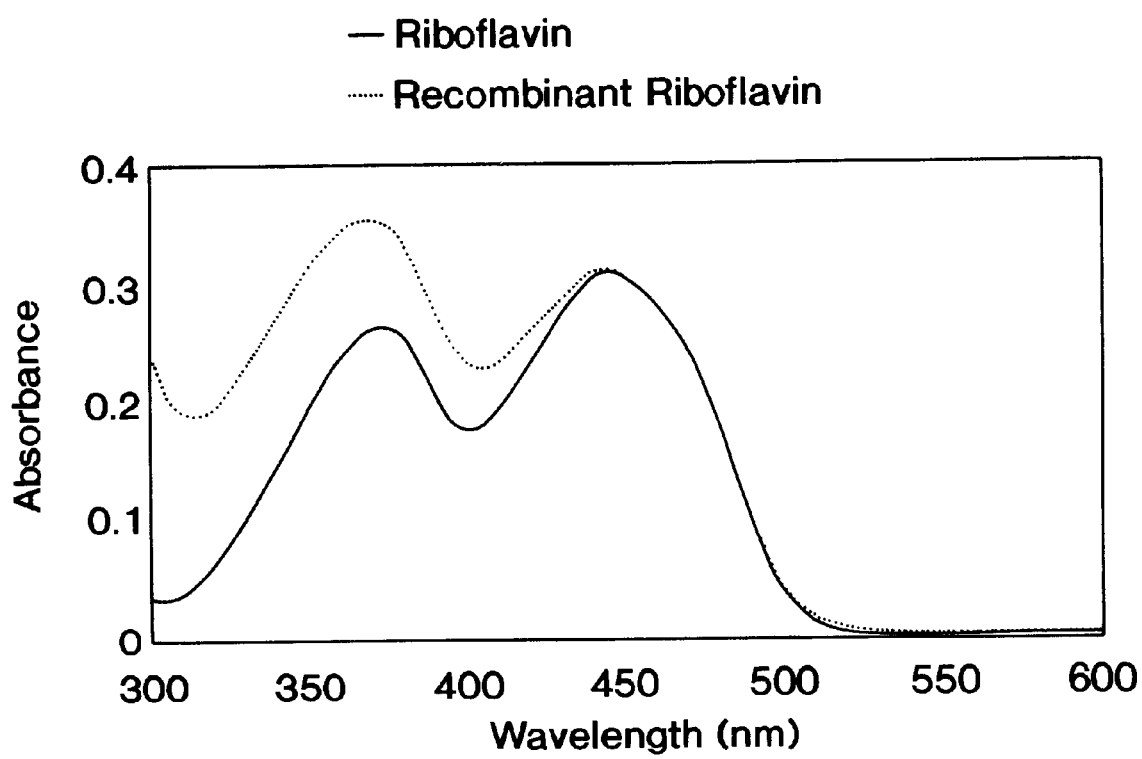
FIGS. 3A and 3B shows the absorbance spectra of aqueous solutions at neutral pH (Panel A) and acidified aqueous solutions (Panel B) of the product excreted into the growth medium by *E. coli* DH5α/pTF10 (solid line) and of a standard riboflavin preparation (dotted line).
Figure 3B:
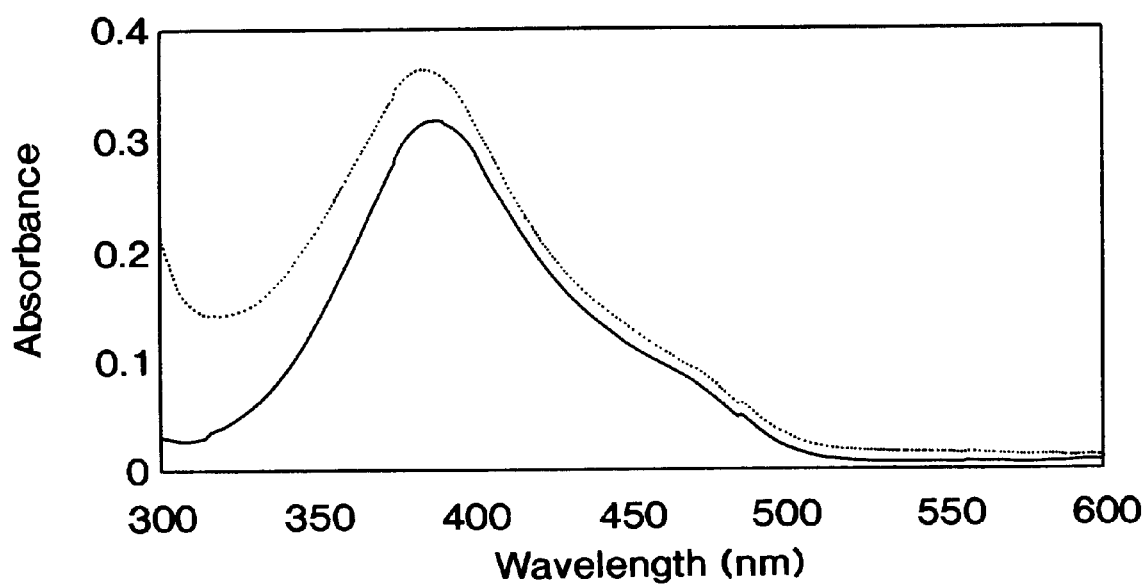

Identification of a riboflavin producing clone. A genomic library of *A. pleuropneumoniae* serotype 5 DNA was constructed in pUC19 and transformed into *E. coli* DH5-α. A single clone, designated pTF10 (FIG. 2), containing a 5.2 kbp insert, was identified that produced a bright yellow extracellular, water-soluble compound that fluoresced under ultraviolet light. The compound was crudely purified by filtration through a 3000 Da cut off membrane filter (Amicon Corporation, Bedford, Mass.). Absorbance spectra of this compound in aqueous solution under neutral conditions showed absorbance peaks at 373 and 443 nm, which coalesced to a single peak at 388 nm under acidic conditions; these results compared well to a riboflavin standard (FIGS. 3A and 3B). Positive and negative ion fast atom bombardment mass spectroscopy indicated that the compound was a flavin (data not shown). Culture of *E. coli* DH5-α/pTF10 in M9 medium plus NZ amine plus 0.6% glucose yielded 10 mg riboflavin per liter in 24 hours. pTF10 was deposited under the terms of the Budapest Treaty at the American Type Culture Collection, 10801 University Boulevard, Manassas, Va. 20110-2209 on Aug. 31, 2000 as ATCC PTA-2438. All restrictions on availability to the public of the deposited material will be irrevocably removed upon granting the patent.

Sequence of APP rib genes. The nucleotide sequence and corresponding predicted amino acid sequence of a 4312 bp region of the insert in pTF10 is shown in FIGS. 4A to 4D. Four open reading frames of 1232, 647, 1205, and 461 bp were observed that encoded proteins with predicted molecular masses of 45,438 Da, 23,403 Da, 44,739 Da and 16,042 Da, respectively. Based on homology with the riboflavin biosynthetic genes of *B. subtilis* (see below), these ORFs were designated ribG, ribB, ribA, and ribH, respectively. All four ORFs were preceded by potential ribosome binding sites (RBS), although the RBS upstream of ribG is not as strong as the other three. Production of riboflavin by this clone is not dependent on its orientation in pUC19 or on induction by IPTG, indicating that it is produced under the control of a native promoter included in the cloned DNA fragment. A consensus promoter sequence of the −35/−10 type (12) was identified within the sequenced region 224 bp upstream from the ribG start codon. A second potential consensus promoter was identified between the genes ribA and ribH. However, no consensus promoter was identified between ribB and ribA, as is found in *B. subtilis*. The ORF encoding ribH is followed by an inverted repeat stem-loop structure with a ΔG=−56.0, that may function as a rho-dependent transcriptional terminator (13).

Homology of APP rib genes. Predicted amino acid sequences of the APP RibGBAH proteins were compared with *B. subtilis* RibGBAH (19); *E. coli* RibA, RibB, RibC, RibG, and ribH (33,34,42); *Photobacterium leiognathi* RibI-III (17), *Photobacterium phosphoreum* RibI-IV (16), and *Vibrio harveyi* LuxH (41) proteins, using the GCG Gap program (Table 1). APP RibG showed 62–63% similarity to the RibG proteins from *B. subtilis* and *E. coli*. APP RibB showed 58–69% and APP RibH showed 69–83% similarity to homologous genes from *B. subtilis*, *E. coli*, and Photobacterium species. APP RibA showed 73% similarity to the entire RibA protein of *B. subtilis* and 61% to the RibII protein of *P. leiognathi*, both of which encode a bifunctional enzyme catalyzing two distinct steps in the riboflavin pathway. In addition, the carboxy terminal half of APP RibA, encompassing ~200 amino acids, shows 59–63% similarity to *E. coli* RibB, and *V. harveyi* LuxH, which encode 3,4-DHBP synthase. The N-terminal region of APP RibA, encompassing the remaining ~200 amino acids, shows 63–73% similarity to *E. coli* RibA and *P. phosphoreum* RibIV, which encode GTP cyclohydrase II.

TABLE 1

Precent similarity of amino acid sequences of riboflavin synthesis proteins[a]
% Similarity with *A. pleuropneumoniae*

| | RibG | | RibB | | RibA | | RibH | |
|---|---|---|---|---|---|---|---|---|
| Bacterium | Compared With | % | Compared With | % | Compared With | % | Compared With | % |
| *B. subtilis* | RibG | 63 | RibB | 69 | RibA | 73 | RibH | 83 |
| *E. coli*[b] | RibG | 62 | RibC | 58 | RibB | 63 | RibH | 74 |
| | | | | | RibA | 73 | | |
| *H. influenzae*[c] | RibG | 58 | RibC | 60 | RibB | 65 | RibE | 75 |
| | | | | | RibA | 71 | | |
| *P. leiognathi* | | NA | RibI | 64 | RibII | 61 | RibIII | 69 |
| *P. phosphoreum*[d] | | NA | RibI | 63 | RibII | 59 | RibIII | 73 |
| | | | | | RibIV | 63 | | |
| *V. harveyi* | | NA | | NA | LuxH | 59 | | NA |

[a]Identity is expressed in percent similarity as calculated by the Genetics Computer Group Needleman-Wunsch algorithm (22). Proteins with partial identify were compared with the entire appropriate *A. pleuropneumoniae* Rib protein.
[b]*E. coli* RibB is homologous to the 5' end of *A. pleuropneumoniae* RibA. *E. coli* RibA is homologous to the 3' end of *A. pleuropneumoniae* RibA.
[c]*H. influenzae* RibB is homologous to the 5' end of *A. pleuropneumoniae* RibA *H. influenzae* RibA is homologous to the 3' end of *A. pleuropneumoniae* RibA.
[d]*P. phosphoreum* RibIV is homologous to the 3' end of *A. pleuropneumoniae* RibA.

Figure 5:
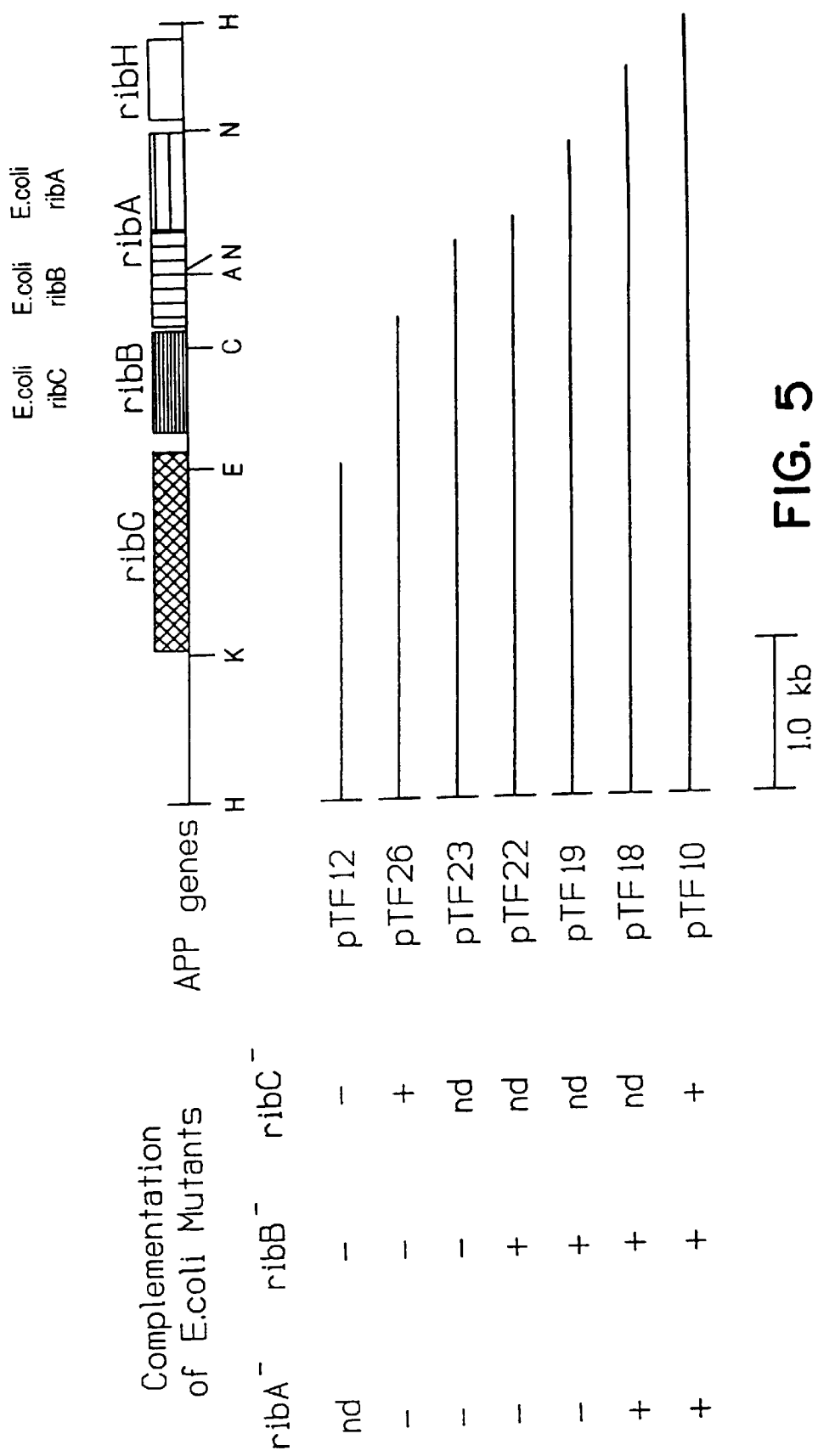
FIG. 5 shows the complementation of *E. coli* riboflavin-requiring mutants by cloned APP rib genes. A physical map for the APP ribGBAH genes is shown as well as several deletions.

Complementation of *E. coli* mutants. The original pTF10 clone and several deletion derivatives were tested for their abilities to complement ribA (GTP cyclohydrase II), ribB (3,4-DHBP synthase), and ribC (β-subunit of riboflavin synthase) mutations in *E. coli* (2) (FIG. 5) Complementation of the *E. coli* mutation was determined by restoration of the ability to grow on M9 minimal medium in the absence of riboflavin. Plasmids containing a complete copy of the APP ribB gene complemented the *E. coli* ribC mutation. Plasmids containing the 5' end of APP ribA complemented the *E. coli* ribB mutation. Plasmids containing a complete copy of APP ribA complemented both *E. coli* ribB and ribA mutations.

Figure 6:
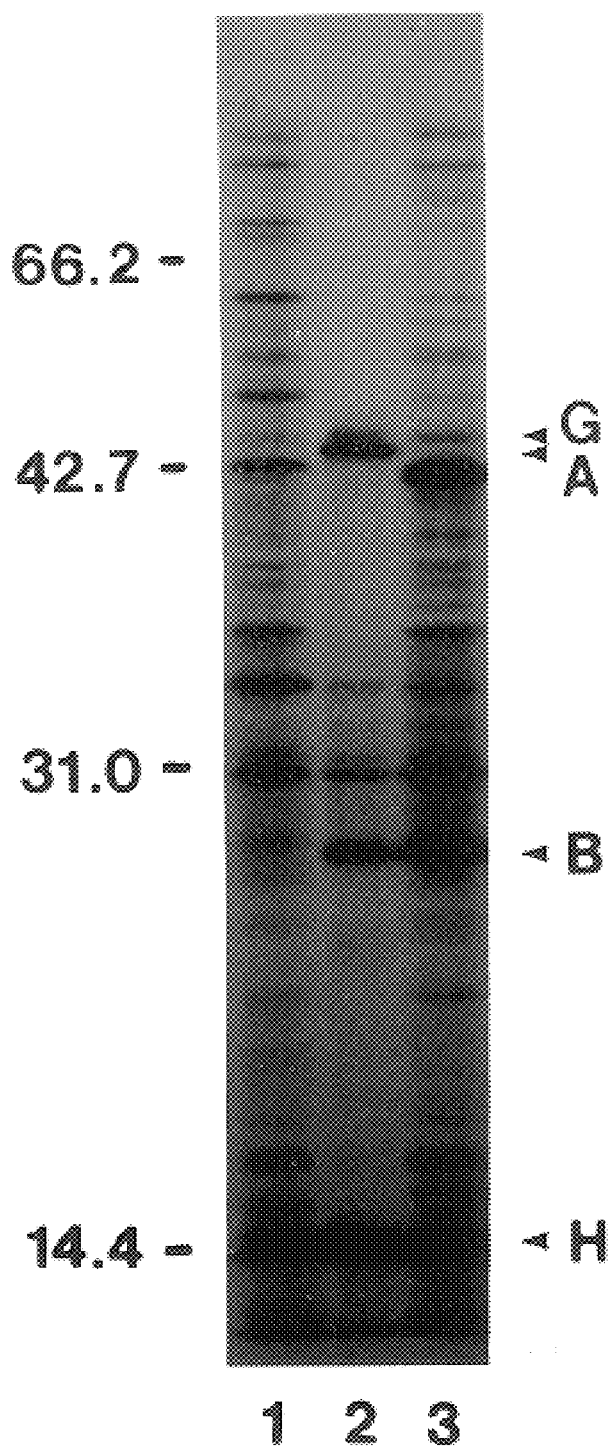
FIG. 6 shows a minicell analysis of the proteins encoded by pTF10 and its deletions.

Minicell analysis. Plasmid pTF10 and its deletion derivatives were transformed into the minicell-producing *E. coli* strain DS410, and the proteins encoded by these plasmids were radioactively labeled, separated by SDS-PAGE, and visualized by autoradiography. Compared with the pUC19 vector, plasmid pTF10 shows four unique proteins with apparent molecular masses of 45 kDa, 27.7 kDa, 43.7 kDa, and 14.8 kDa (FIG. 6), which correspond well with the sizes predicted for the RibG, RibB, RibA, and RibH proteins by amino acid sequence data. The RibG protein did not appear to be as strongly expressed as RibB, RibA, and RibH. Analysis of proteins encoded by plasmid pTF19 (FIG. 5), which contains no ribH and a slightly truncated ribA gene, eliminates the 14.8 kDa protein (RibH) and truncates the 43.7 kDa protein (RibA) to 42.5 kDa (FIG. 6). Plasmid pTF12 (FIG. 5), which does not contain ribB, ribA, or ribH genes, does not express the 27.7, 43.7, or 14.8 kDa proteins (data not shown).

Described above is the identification, cloning and complete nucleotide sequence of four genes from *Actinobacillus pleuropneumoniae* that are involved in riboflavin biosynthesis. The cloned genes can specify production of large amounts of riboflavin in *E. coli*, can complement several defined genetic mutations in riboflavin biosynthesis in *E. coli*, and are homologous to riboflavin biosynthetic genes from both *E. coli* and *Bacillus subtilis*. The genes have been designated APP ribGBAH due to their similarity in both sequence and arrangement to the *B. subtilis* ribGBAH operon.

The DNA sequence data, complementation, and minicell analysis strongly suggest that the four rib genes are transcribed from a single APP promoter upstream of the ribG gene. This promoter, among the first described for housekeeping genes in APP, is a good match for an *E. coli* consensus −35/−10 promoter. There is a 4 of 6 bp match at the −35 region, a 17 bp interval, a 4 of 6 bp match at the −10 region, an 8 bp interval, and a CAT box at the −1/+1 site. There is also a second potential promoter located between ribA and ribH, although it is not clear whether this promoter is functional.

Biosynthesis of riboflavin by APP appears to be more similar to that in the gram-positive bacterium *B. subtilis* than in the gram-negative bacterium *E. coli*. First, APP rib genes are arranged in an operon similar to that seen in B. subtilis, rather than scattered throughout the chromosome as is found in *E. coli*. However, the *B. subtilis* rib operon contains a fifth gene, ribT, that is proposed to mediate the third step in riboflavin biosynthesis; it is unlikely that a ribT homologue is present as part of the operon in APP because of the presence of a strong inverted repeat following ribH and the lack of a likely reading frame downstream. Second, APP contains a ribA gene that encodes a bifunctional enzyme with both GTP cyclohydrase II and DHPB synthase activities, as is found in *B. subtilis; E. coli* has two genes, ribA and ribB, that encode these two enzymes separately. Finally, the APP riboflavin biosynthetic enzymes are more similar at the amino acid level to the enzymes of *B. subtilis* than to those of *E. coli*, although alignment of the proteins from all three sources shows highly conserved sequences (data not shown).

It should be noted that in three bioluminescent species from the family Vibrionaceae, *Vibrio harveyi, Photobacterium leiognathi*, and *P. phosphoreum*, riboflavin biosynthesis genes have been shown to be closely linked to the lux operon (10, 11, 41). $FMNH_2$ is the substrate for the light-emitting reaction, and therefore an increase in bioluminescence requires an increased supply of the cofactor. Since riboflavin is the precursor for FMN, linkage and possibly coordinate regulation of lux and rib genes may facilitate the expression of bioluminescence in these bacteria.

The recombinant *E. coli* DH5-α containing plasmid pTF10 showed a marked increase in extracellular riboflavin production, most likely due to the lack of regulation (40) and high copy number of the cloned synthetic genes (45). Although the APP rib operon is similar in structure to that of *B. subtilis*, it is not yet known whether the genes are tightly regulated in APP by a repressor similar to *B. subtilis* RibC, or whether they are constituitively expressed as appears to be true in *E. coli* (33). It is believed APP must synthesize riboflavin to meet its own metabolic demands during infection, since riboflavin is not synthesized by mammals and therefore is not likely to be freely available to APP within its porcine host.

Attenuation of Rib-Mutants of *A. pleuropneumoniae*

Applicants have constructed deletion-disruption riboflavin-requiring mutants of *A. pleuropneumoniae* serotypes 1 and 5.

Applicants have conducted experiments to confirm that the Rib-APP mutants constructed are attenuated in swine.

In a preliminary experiment, seven 8-to-10 week old pigs were used. Three pigs were infected endobronchially with $Nal^R$ (resistant to the antibiotic malidixic acid) derivatives of wild type virulent APP-1 or APP-5; three were infected with APP-5 Rib-mutants; and one was used as an uninfected control. The APP strains, dosages used for infection, and results are summarized below in Table 2. Animals were euthanized when clinical signs became severe or at 12 hours post infection. The animals were necropsied and the lungs examined for gross pathology and histopathology, and lungs were cultured to recover APP.

TABLE 2

Summary of clinical signs, gross pathology, and histopathology seen in pigs challenged with either wide type APP serotype 1 or 5 or Rib- mutants of App Serotype 5

| APP Strain and Description | Dosage | Results |
|---|---|---|
| AP225: APP-1, $Nal^R$ | $2 \times 10^8$ cfu | Died, <4 hrs; 4+ peracute hemorrhagic pneumonia lesions |
| AP227: APP-5, $Nal^R$ | $1 \times 10^9$ cfu | Died, <4 hrs: 4+ peracute hemorrhagic pneumonia lesions |
| AP228: APP-5, $Nal^R$ | $1 \times 10^9$ cfu | Died, <4 hrs: 4+ peracute hemorrhagic pneumonia lesions |
| AP229: APP-5, $Nal^R$, $Km^R$, Rib- | $1 \times 10^9$ cfu | Mild clinical signs; 1+ mild pneumonia lesions |
| AP230: APP-5, $Nal^R$, $Km^R$, Rib- | $1 \times 10^9$ cfu | Mild clinical signs; 1+ mild pneumonia lesions |
| AP231: APP-5, $Nal^R$, $Km^R$, Rib- | $1 \times 10^9$ cfu | Mild clinical signs; 1+ mild pneumonia lesions |
| None | — | 1+ mild pneumonia lesions (mycoplasma?) |

Note that the dosage used in all of these animals was about 200 times the $LD_{50}$(50% lethal dose, or the dose that will kill 50% of the animals exposed) for the wt (wild type)

APP parent strains. The Nal$^R$ derivatives of the wild type) parent strains retained virulence, triggering severe fibrino-suppurative hemorrhagic pneumonia and death within 4 hours. The Rib- mutants caused minimal clinical signs (increased respiration rate and slight fever) and at most mild signs of pneumonia, including some consolidation but no hemorrhagic necrosis, as compared to the uninfected control. These were not SPF (specific pathogen free) pigs, and there were histologic lesions suggestive of mild mycoplasma infection, in all of the pigs, including the uninfected control (Table 2).

Described below is the construction of a deletion-disruption riboflavin mutant of A. pleuropneumoniae serotype 1 (APP-1) and detailed analysis of the attenuation of this APP-1 Rib-mutant in vivo in swine.

Materials and Methods

Bacterial strains and media. The bacterial strains and plasmids used in this study are listed in Table 1. *A. pleuropneumoniae* strains were cultured at 37° C. in either brain heart infusion (BHI), heart infusion (HI), or tryptic soy agar (TSA) (Difco Laboratories, Detroit, Mich.) containing 10 μg/ml NAD (V factor) (Sigma Chemical Company, St. Louis, Mo.). Riboflavin (Sigma) was added to a final concentration of 200 μg/ml when needed. *E. coli* strains were cultured in Luria-Bertani medium. Ampicillin was added to 100 μg/ml and kanamycin to 50 μg/ml for plasmid selection in *E. coli* strains. For *A. pleuropneumoniae* strains, 50 μg/ml kanamycin sulfate and 25 μg/ml nalidixic acid were added as required, except for selection after matings which were performed with 100 μg/ml kanamycin sulfate and 50 μg/ml nalidixic acid.

DNA manipulations. DNA modifying enzymes were supplied by Boehringer-Mannheim Biochemicals (Indianapolis, Ind.) and used according to the manufacturer's specifications. Genomic DNA was prepared according to the lysis/proteinase K method of the Gene Fusion Manual (Silhavy, T. J. 1984. DNA extraction from bacterial cells. p. 137–139. In Experiments with Gene Fusions. Cold Spring Harbor Laboratory, Cold Spring Harbor, N.Y. 34). Plasmid DNA preparations, agarose gel electrophoresis, and *E. coli* transformation were all performed by conventional methods (Sambrook, J., E. F. Fritsch and T. Maniatis. 1989. Molecular Cloning: A Laboratory Manual, 2nd. ed. Cold Spring Harbor Press, Cold Spring Harbor, N.Y.).

Filter mating targeted mutagenesis. Filter mating between *E. coli* S17-1 (λpir)/pTF67A and AP225 was performed according to the protocol of Mulks and Buysse (Mulks, M. H. and J. M. Buysse. 1995. A targeted mutagenesis system for *Actinobacillus pleuropneumoniae.* Gene 165:61–66). Briefly, bacterial cultures were grown overnight at 37° C. Equal cell numbers of donor and recipient cultures, as determined by optical density at 520 nm, were added to 5 ml 10 mM $MgSO_4$ and the bacteria pelleted by centrifugation. The pellet containing the cell mating mixture, resuspended in 100 μl of 10 mM $MgSO_4$, was plated on a sterile filter on BHIV+riboflavin agar and incubated for 3 h at 37° C. Cells were washed from the filter in sterile phosphate buffered saline (pH 7.4), centrifuged, resuspended in 400 μl BHIV broth and plated in 100 μl aliquots on BHIV containing riboflavin, kanamycin, and nalidixic acid. Kanamycin and nalidixic acid resistant colonies were selected from filter mating plates and screened for riboflavin auxotrophy by replica plating onto TSAV, observing for inability to grow in the absence of added riboflavin.

Southern Analysis of Transconjugants. Chromosomal DNA and plasmid controls were digested with the appropriate restriction enzymes and the DNA fragments were separated on an 0.7% ultrapure agarose gel in TAE buffer. Southern blots were performed as described by Sambrook et al (Sambrook, J., E. F. Fritsch and T. Maniatis. 1989. Molecular Cloning: A Laboratory Manual, 2nd. ed. Cold Spring Harbor Press, Cold Spring Harbor, N.Y.). DNA probes were labeled with digoxygenin by random priming using the Genius V. 3.0 kit from Boehringer Mannheim. Probes included the 5.2 Kb insert from pTF10 containing the intact riboflavin operon from AP106 (Rib), the 1.4 Kb ClaI/NdeI fragment deleted from the riboflavin operon in the construction of pTF67a (R.Del.), the 1.2 Kb kanamycin cassette from pUC4K (Km) and the intact plasmid pGP704 (pGP704). Hybridization was carried out in 50% formamide at 42° C. for 16 h. Blots were washed twice in 2×SSC/0.1% SDS for 15 min at room temperature, then twice in 0.1× SSC/0.1% SDS for 30 min at 65° C. Blots were developed with alkaline phosphatase-conjugated anti-digoxygenin and colorimetric substrate (Boehringer Mannheim) according to the manufacturer's instructions.

Phenotypic analysis of mutant strains. Whole cell lysates and supernatants of AP100, AP225 ($Nal^R$), and AP233 ($Km^R$, $Nal^R$, Rib-) were prepared from overnight cultures grown in HIV+5 mM $CaCl_2$+appropriate antibiotics. APP225 and APP33 were deposited under the terms of the Budapest Treaty at the American Type Culture Collection on Aug. 31, 2000 as ATCC PTA-2429 and ATCC PTA-2430, respectively. All restrictions on availability to the public of the deposited material will be irrevocably removed upon granting the patent. Cells were separated by microcentrifugation and resuspended in SDS-PAGE sample buffer (Laemnli, U.K. 1970. Cleavage of structural proteins during the assembly of the head of bacteriophage T4. Nature 227:680–685). The culture supernatant was precipitated with an equal volume of 20% trichloroacetic acid (TCA) and resuspended in SDS-PAGE (sodium dodecyl sulfate-polyacrylamide gel electrophoresis) sample buffer. Cellular polysaccharides, including lipopolysaccharide (LPS) and capsular polysaccharide, were prepared according to the cell lysis/proteinase K method of Kimura et al (Kimura, A. and E. J. Hansen. 1986. Antigenic and phenotypic variations of *Haemophilus influenzae* type B lipopolysaccharide and their relationship to virulence. Infect. Immun. 51:69–79) . All samples were analyzed on a 0.125% SDS-12% acrylamide gel using a discontinuous buffer system (Laemmli, U.K. 1970. Cleavage of structural proteins during the assembly of the head of bacteriophage T4. Nature 227:680–685). Samples were transferred to nitrocellulose according to standard protocols (Sambrook, J., E. F. Fritsch and T. Maniatis. 1989. Molecular Cloning: A Laboratory Manual, 2nd. ed. Cold Spring Harbor Press, Cold Spring Harbor, N.Y.) and probed with convalescent serum from a pig infected with *A. pleuropneumoniae* serotype 1. Antigen-antibody complexes were detected with horseradish peroxidase-conjugated protein A (Boehringer Mannheim) and the calorimetric substrate 4-chloro-naphthol (BioRad, Hercules, Calif.).

Production of serotype-specific capsular polysaccharide was measured by coagglutination assay using hyperimmune rabbit anti-sera complexed to *Staphylococcus aureus* whole cells (Jolie, R. A. V., M. H. Mulks, and B. J. Thacker. 1994. Antigenic differences within *Actinobacillus pleuropneumoniae* serotype 1. Vet. Microbiol. 38:329–349).

Electroporation of *A. pleuropneumoniae.* AP233 was grown in 100 ml BHIV with riboflavin at 37° C., with shaking at 150 RPM, to an $OD_{520}$ of 0.7. Cells were chilled on ice and centrifuged at 5,000×g at 4° C. for 10 min. Cells were washed twice in ice cold sterile 15% glycerol. Cells were resuspended in 2 ml 15% glycerol and frozen in 50 μl aliquots using a dry ice-ethanol bath. Plasmid DNA was added to an aliquot of competent cells thawed on ice and then transferred to a 0.1 cm gap electroporation cuvette (BioRad). Cells were electroporated using a Gene Pulser II (BioRad) with the following settings: voltage, 1.8 kV; resistance, 200Ω; capacitance, 25 μFd.

Experimental infections. Eight-week-old, specific-pathogen-free, castrated, male pigs (Whiteshire Hamroc, Inc., Albion, Ind.) were allotted to six challenge groups by a stratified random sampling procedure, balancing each group for body weight. Each challenge group was housed in a separate BSL-2 (biosafety level) isolation room at the Michigan State University Research Containment Facility. All experimental protocols for animal experiments were reviewed by the Michigan State University All University Committee on Animal Use and Care, and all procedures conformed to university and USDA regulations and guidelines.

For preparation of challenge inocula, bacteria were grown in 30 ml HIV+5 mM $CaCl_2$+riboflavin and antibiotics as needed, in 300 ml baffled side-arm flasks, at 37° C. with shaking at 160 RPM, to an $OD_{520}$ (optical density) of 0.8. Ten ml of each culture was harvested by centrifugation at room temperature and washed once with sterile 0.9% saline. The cell pellet was resuspended in 10 mL of saline and diluted in saline to obtain the desired cfu/ml. The actual inoculating doses were retrospectively calculated by viable cell counts on agar plates.

For the challenge procedure, pigs were anesthetized by intravenous injection with ketamine (4.4 mg/kg) and xylazine (1.65 mg/kg) and inoculated by percutaneous intratracheal injection with the appropriate dose of bacteria suspended in 10 mL saline. Clinical signs of pleuropneumonia, including increased respiration rate, fever, dyspnea, decreased appetite and activity/attitude (depression), were monitored and scored as previously described (Jolie, R. A. V., M. H. Mulks, and B. J. Thacker. 1995. Cross-protection experiments in pigs vaccinated with *Actinobacillus pleuropneumoniae* subtypes 1A and 1B. Vet. Microbiol. 45:383–391). Seriously ill animals, as determined by severe dyspnea and/or depression, were euthanized immediately. Survivors were euthanized three days post-challenge. All animals were necropsied, and lungs were examined macroscopically for *A. pleuropneumoniae* lesions, including edema, congestion, hemorrhage, necrosis, abscessation, fibrosis, and pleuritis. The percentage of lung tissue and pleural surface area affected was estimated for each of the seven lung lobes, and the total % pneumonia and % pleuritis calculated using a formula that weights the contribution of each lung lobe to the total lung volume (Jolie, R. A. V., M. H. Mulks, and B. J. Thacker. 1995. Cross-protection experiments in pigs vaccinated with *Actinobacillus pleuropneumoniae* subtypes 1A and 1B. Vet. Microbial. 45:383–391). Representative lung samples were collected for histopathology and for bacterial culture.

Results

Figure 7:
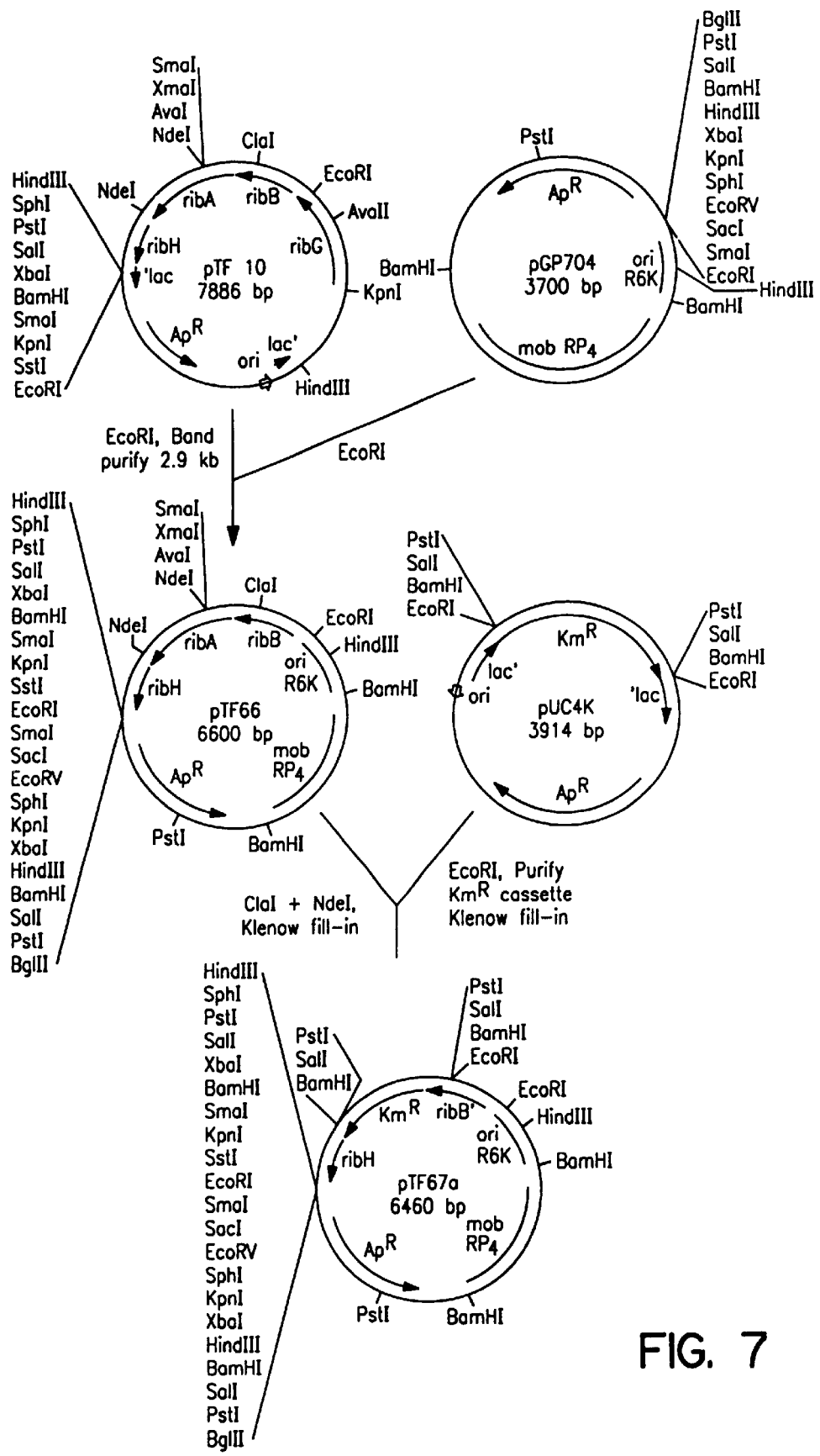
FIG. 7 shows the construction of pTF67a, a suicide delivery vector containing a portion of the APP rib operon with a part of ribB and all of ribA deleted and replaced with a gene cassette encoding resistance to the antibiotic kanamycin.

Construction of *A. pleuropneumoniae* rib mutants. To construct riboflavin-requiring auxotrophic mutants of *A. pleuropneumoniae*, a suicide plasmid with part of the riboflavin operon deleted and replaced with a kanamycin-resistance ($Km^R$) cassette was designed (FIG. 7). A 2.9 kb EcoRI fragment from pTF10 (Fuller, T. E. and M. H. Mulks. 1995. Characterization of *Actinobacillus pleuropneumoniae* riboflavin biosynthesis genes. J. Bacteriol. 177:7265–7270) containing the *A. pleuropneumoniae* ribBAH genes was cloned into the EcoRI site of the conjugative suicide vector pGP704 (18) to create plasmid pTF66. pTF66 was deposited under the terms of the Budapest Treaty at the American Type Culture Collection on Aug. 31, 2000 as ATCC PTA-2437. All restrictions on availability to the public of the deposited material will be irrevocably removed upon granting the patent. pTF66 was digested with ClaI and NdeI to excise the 3' end of ribB and the entire ribA gene. After Klenow treatment of the DNA, the 1.2 kb $Km^R$ cassette, excised with EcoRI from pUC4K, was blunt-end ligated into the rib deletion site to create pTF67a.

pTF67a was transformed into *E. coli* S17-1 (λpir) and mobilized into AP225 ($Nal^R$) to produce >100 transconjugant colonies demonstrating resistance to both nalidixic acid and kanamycin. Transconjugants were replica plated onto TSAV and TSAV+riboflavin to assess the requirement for riboflavin and the stability of the riboflavin auxotrophy. Two classes of transconjugants were found. The majority of the transconjugants, e.g. AP234, were unstable and produced revertants capable of growth without supplemental riboflavin in the absence of kanamycin selection. One transconjugant, AP233, was very stable, maintaining kanamycin resistance as well as the inability to grow without exogenous riboflavin. All transconjugants were confirmed as *A. pleuropneumoniae* by gram stain, colonial morphology, and requirement for V factor (β-NAD).

Figure 8A:
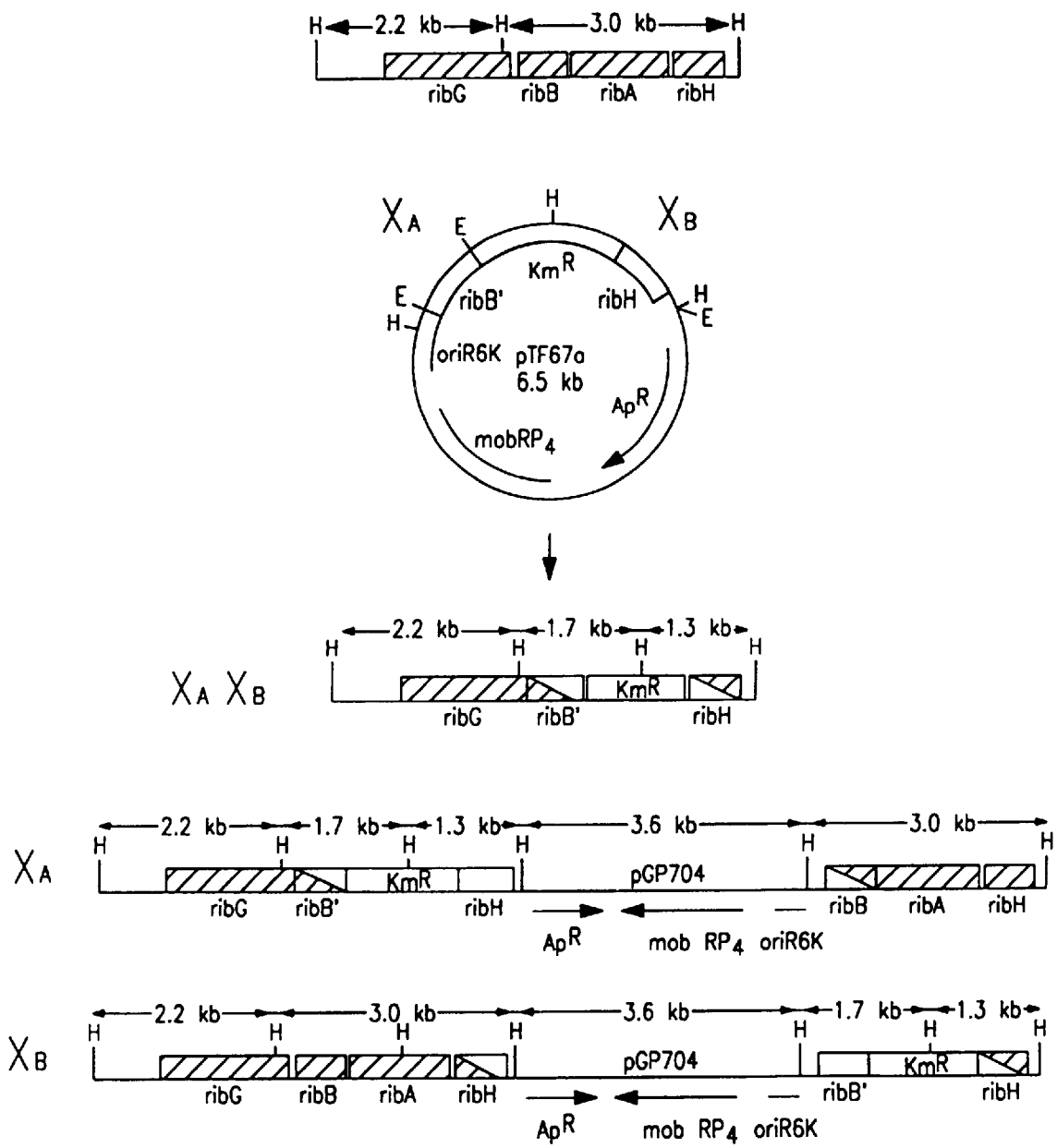
FIG. 8A is an analysis of rib-transconjugants of *A. pleuropeneumoniae* serotype 1 .
Figure 8B:
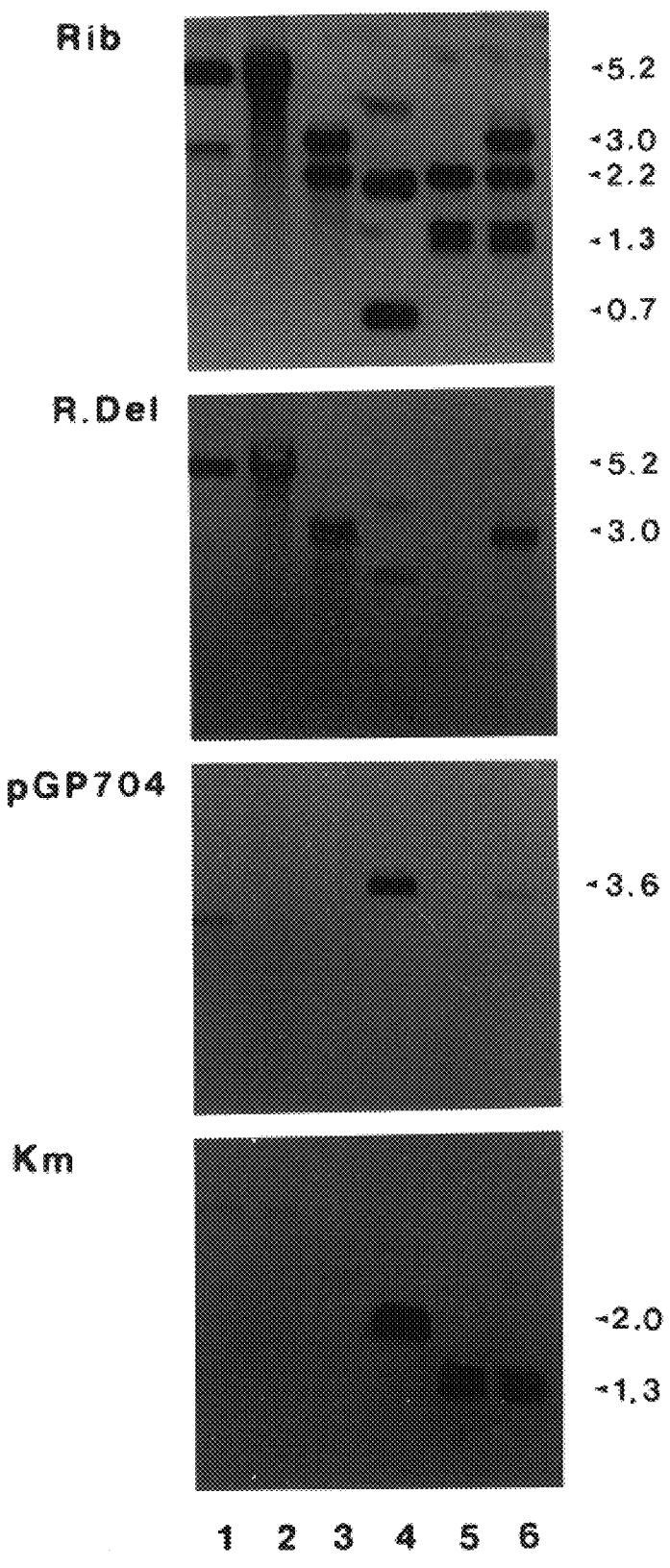
FIG. 8B is a southern blot analysis of chromosomal DNA from *A. pleuropneumoniae* serotype 1 rib mutants.

Southern blot analysis of transconjugants. Two transconjugants were selected for further analysis based on their phenotypes as potential single (AP234) and double cross-over mutants (AP233). Southern blot analysis of transconjugant genomic DNA from the two mutants indicated that AP233 and AP234 were indeed double and single cross-over insertion mutants respectively (FIG. 8A). Predicted band sizes for single and double cross-over events are shown in FIG. 8A. Genomic DNA from AP233 contained a 2.2 Kb HindIII fragment that hybridized with the riboflavin operon (Rib) probe, as well as 1.7 and 1.3 Kb fragments that hybridized with both the Rib and Km probes; however, there was no reaction with either pGP704 nor the deleted portion of the riboflavin operon (FIG. 8B). This is the pattern of hybridization predicted in transconjugants that replaced the wild type riboflavin operon with the mutated rib::$Km^R$ locus by a double-crossover event (FIG. 8A). In contrast, genomic DNA from AP234 shows the presence of DNA homologous to the fragment deleted from the riboflavin operon (R. del), pGP704, and the kanamycin cassette (FIG. 8B). This is the pattern of hybridization predicted in transconjugants that inserted the entire pTF67a plasmid into the wild type rib operon by a single crossover event (FIG. 8A).

Phenotypic analysis of the *A. pleuropneumoniae* rib mutant. Whole cell lysates, TCA-precipitated culture supernatants, and polysaccharide preparations were analyzed on silver stained SDS-PAGE and on immunoblots developed with convalescent swine sera. No differences in protein, LPS, extracellular toxin, or capsular polysaccharide profiles were detected between wild type AP100, its $Nal^R$ derivative AP225, and the riboflavin mutant AP233 (data not shown). There was no difference in reactivity with serotype-specific antisera as determined by coagglutination assay (data not shown).

Complementation of the rib mutation with a cloned wild type rib operon. The 5.2 Kb insert from pTF10, containing the wild-type *A. pleuropneumoniae* riboflavin operon, was cloned into pGZRS19, an *E. coli-A. pleuropneumoniae* shuttle vector (West, S. E. H., M. J. M. Romero, L. B . Regassa, N. A. Zielinski, and R. A. Welch. 1995. Construction of *Actinobacillus pleuropneumoniae-Escherichia coli* shuttle vectors: expression of antibiotic resistance genes. Gene 160: 81–86), to form pTF76. pTF76 was deposited under the terms of the Budapest Treaty at the American Type Culture Collection on Aug. 31, 2000 as ATCC PTA-2436. All restrictions on availability to the public of the deposited material will be irrevocably removed upon granting the patent. pTF76 was transformed into AP233 by electroporation, restoring the ability of AP233 to grow in the absence of exogenous riboflavin and restoring the virulence of the mutant (see below).

Attenuation of virulence of the rib mutant in swine. Six groups of three pigs each were infected with: group 1, 1 $LD_{50}$ ($5\times10^6$ cfu) of AP225; groups 2–5, AP233 at doses equivalent to 4, 20, 100, and 500 times the wild-type $LD_{50}$; and group 6, 1 wild-type $LD_{50}$ of AP233/pTF76. Mortality, lung score, and clinical score data, shown in Tables 3, 4 and 5, all indicate that the riboflavin auxotroph is avirulent in pigs at doses as high as 500 times the wild-type $LD_{50}$. The pigs infected with the rib mutant AP233 displayed no dyspnea, elevated respiration rate, depression, or loss of appetite, and had no typical pleuropneumonic pathology at necropsy, at even the highest dose tested. In contrast, 1 of 3 pigs infected with the wild-type AP225 strain died, and all three exhibited significant clinical signs of APP disease, including elevated respiration rates, dyspnea, depression, loss of appetite, and fever, and severe pneumonia and pleuritis was evident at necropsy. Pigs infected with AP233 containing the riboflavin genes in trans (pTF76) also exhibited obvious clinical signs and significant pneumonia and pleuritis, although somewhat less severe than the wild-type strain. These results indicate that restoration of the ability to synthesize riboflavin does restore virulence.

Bacteria were readily reisolated at necropsy from the lungs of pigs receiving AP225 and AP233/pTF76. All reisolated organisms were characterized by gram stain, colonial morphology, requirement for V factor (β-NAD), antibiotic sensitivity, and serotyping by coagglutination. Reisolated organisms showed no differences from the initial inocula, including the presence of plasmid pTF76 in bacteria reisolated from pigs infected with AP233/pTF76. In contrast, we were unable to recover organisms from the lungs of animals infected with AP233 and euthanized 48 hours post infection.

TABLE 3

Characteristics of bacterial strains and plasmids

| Strain/Plasmid | Characteristics | Source/Reference |
|---|---|---|
| Strain | | |
| *E. coli* DH5-α | supE44, ΔlacU169, (φ80lacZΔM15), hsdR17, recA1, endA1, gyrA96, thi-1, relA1 | BRL (USA) |
| *E. coli* DH5-α (λpir) | λpir, supE44, ΔlacU169, (λ80lacZΔM15), hsdR17, recA1, endA1, gyrA96, thi-1, relA1 | Mulks & Buysse |
| *E. coli* S17-1 (λpir) | λpir, recA, thi, pro, hsd, (r-m+), RP4-2, (Tc::Mu), (Km::Tn7), [TmpR], [SmR] | Simon et al. |
| AP100 | *A. pleuropneumoniae* ATCC 27088, | ATCC |

TABLE 3-continued

Characteristics of bacterial strains and plasmids

| Strain/Plasmid | Characteristics | Source/Reference |
|---|---|---|
| | serotype 1, passaged through pigs | |
| AP106 | *A. pleuropneumoniae* ISU178, a serotype 5 field isolate, passed through pigs | Iowa State University |
| AP225 | A spontaneous nalidixic acid resistant mutant of AP100 | This work |
| AP233 | A double cross-over riboflavin auxotroph of AP225 | This work |
| AP234 | A single cross-over riboflavin auxotroph of AP225 | This work |
| Plasmid | | |
| pUC19 | $Ap^R$ cloning vector | Vieira & Messing |
| pUC4K | $Ap^R$, $Km^R$ vector, source of the kan cassette | Pharmacia (USA) |
| pGP704 | $Ap^R$ broad host range suicide vector | Miller & Mekalanos |
| pGZRS19 | $Ap^R$ APP-*E. coli* shuttle vector | West et al. |
| PTF10 | AP106 ribGBAH genes cloned into pUC19 | Fuller & Mulks |
| pTF66 | A 2.9 kb fragment containing AP106 ribBAH in pGP704 | This work |
| pTF67a | pTF66 with all of ribA and part of ribB deleted and replaced with the kan cassette from pUC4K | This work |
| pTF76 | 5.2 Kb insert from pTF10 cloned into pGZRS19 | This work |

TABLE 4

Mortality and Lung Lesion Data

| Group | Strain | Dose $(LD_{50})^a$ | Mortality | % Pneumonia[b] | % Pleuritis[c] |
|---|---|---|---|---|---|
| 1 | AP225 (WT) | 1 | 1/3 | 66.7 | 71.7 |
| 2 | AP233 (Rib-) | 4 | 0/3 | 0 | 0 |
| 3 | AP233 (Rib-) | 20 | 0/3 | 0 | 0 |
| 4 | AP233 (Rib-) | 100 | 0/3 | 0 | 0 |
| 5 | AP233 (Rib-) | 500 | 0/3 | 0 | 0 |
| 6 | AP233 + pTF76 | 1 | 0/3 | 27.6 | 20.2 |

[a]Doses are multiples of the established wild-type APP 225-serotype 1 $LD_{50}$ of $5.0 \times 10^6$ cfu (12)
[b]Percentage of lung tissue exhibiting *A. pleuropneumoniae* lesions
[c]Percentage of pleural surface area exhibiting pleuritis

TABLE 5

Clinical Score Data

| Group | Strain | Dose (LD$_{50}$)[a] | RR Max[b] | Temp Max[c] | Dyspnea[d] | Depression[e] | Appetite[f] |
|---|---|---|---|---|---|---|---|
| 1 | AP225 | 1 | 20 | 105.7 | 5.5 | 6.7 | 4.2 |
| 2 | AP233 | 5 | 8 | 102.5 | 0 | 0 | 0 |
| 3 | AP233 | 20 | 8 | 103.3 | 0 | 0 | 0 |
| 4 | AP233 | 100 | 8 | 103.5 | 0 | 0 | 0 |
| 5 | AP233 | 500 | 8 | 102.8 | 0 | 0 | 0 |
| 6 | AP233 + pTF76 | 1 | 19.3 | 105.4 | 4.5 | 4.7 | 3.7 |
| | Normal | | 8.0 | <103.0 | 0 | 0 | 0 |
| | Maximum | | 25 | | 15 | 15 | 5 |

[a]Doses are multiples of the established wild-type APP225-serotype 1 LD$_{50}$ of 5.0 × 10$^6$ cfu (12)
[b]Maximum respiratory rate observed after challenge. Respiratory rate recorded as number of breaths per 15 sec observation period.
[c]Maximum rectal temperature after challenge, in degrees Fahrenheit.
[d]Dyspnea score measures degree of respiratory distress and labored breathing. Scored as 0 = normal; 1 = slight; 2 = moderate; 3 = severe. Total score = sum of scores taken at 12 hour intervals after challenge.
[e]Depression score evaluates attitude and activity. Scored as 0 = normal; 1 = slight inactivity; 2 = moderate; 3 = severe. Total score = sum of scores taken at 12 hour intervals after challenge.
[f]Appetite was scored as 0 = did eat; 1 = did not eat. Total score = number of 12 hour periods not eating over 60 hour observation period.

Discussion

Above is shown the construction of a serotype 1 *Actinobacillus pleuropneumoniae* deletion-disruption riboflavin mutant that is attenuated in vivo. The *A. pleuropneumoniae* ribGBAH operon was disrupted by deleting an internal segment of the operon (ribBA) and replacing it with a Km$^R$ cassette using a targeted mutagenesis technique (Mulks, M. H. and J. M. Buysse. 1995. A targeted mutagenesis system for *Actinobacillus pleuropneumoniae*. Gene 165:61–66) A stable riboflavin-requiring, Km$^R$ mutant, AP233, was phenotypically identical to its wild-type parent based on analysis of proteins, extracellular toxin, LPS, and capsular polysaccharide by SDS-PAGE, immunoblot, and coagglutination.

A riboflavin mutant of *A. pleuropneumoniae* serotype 5 was also constructed and was also found to be attenuated in a preliminary animal challenge experiment. However, further studies were conducted in serotype 1 because serotype 5 seemed to be very resistant to transformation by standard heat shock or electroporation procedures. In order to complement the rib mutation in trans, and for ease of future genetic manipulations, it was desirable to use a serotype 1 strain for these studies.

Experimental infection of pigs, the only natural host for *A. pleuropneumoniae*, demonstrated that the riboflavin-requiring mutant was unable to cause disease at dosages as high as 500 times the LD$_{50}$ for the wild-type parent. In the four groups of pigs infected with AP233 by intratracheal inoculation, there was no mortality, no significant clinical signs were observed, and no typical pleuropneumonic lesions were observed at necropsy. Complementation of AP233 in trans with the wild-type *A. pleuropneumoniae* riboflavin operon restored both the ability to grow without exogenous riboflavin and virulence, demonstrating that the riboflavin mutation itself is responsible for the attenuation in vivo.

It is important to note that the riboflavin-requiring mutant used in these studies is a deletion mutant, with ~1.4 Kb of the riboflavin operon removed from the chromosome and replaced with an antibiotic resistance marker. Neither reversion to prototrophy nor loss of kanamycin resistance in this mutant in the laboratory was observed. In the preliminary experiment with a serotype 5 riboflavin mutant, it was possible to reisolate the mutant from the lungs at 16 hours post-infection. All colonies isolated in this experiment were kanamycin-resistant, nalidixic acid-resistant, and riboflavin requiring, suggesting that reversion to prototrophy and thus virulence will not occur in vivo.

In the dosage trial experiment, AP233 was not recovered from the lungs of infected swine at 48 hours post-infection. These results may indicate poor persistence of the organism in vivo. If necessary, sufficient exogenous riboflavin could be added to the vaccine to allow the organism to replicate minimally and therefore persist long enough to induce a protective immune response. The above represents a new addition to the group of biosynthetic mutations that can be used to construct attenuated strains of bacteria. It also shows a genetically modified attenuated mutant of APP that is capable of production of all of the major virulence factors of this organism, including extracellular toxins and capsular polysaccharide.

Evaluation of a Riboflavin-Requiring Auxotrophic Mutant of *Actinobacillus pleuropneumoniae* as a Genetically Defined Live Attenuated Vaccine Against Porcine Pleuropenumonia The applicants have evaluated a genetically defined riboflavin-requiring attenuated mutant of *Actinobacillus pleuropneumoniae* as a live avirulent vaccine that provides immunity against experimental challenge with a virulent strain of *A. pleuropneumoniae*.

The specific aims of this study were: 1) to evaluate whether respiratory exposure to a live attenuated vaccine APP strain elicits protection against subsequent experimental challenge with virulent *A. pleuropneumoniae*; and 2) to determine whether addition of exogenous riboflavin to the vaccine dosage improves persistence, and therefore immunogenicity and protection; and 3) to compare the protection afforded by respiratory exposure to that elicited by intramuscular (IM) immunization with the live vaccine, which is a more commercially feasible vaccination route.

Materials and Methods

Animals. In this study, 6-to-8 week old crossbred (Yorkshire/Landrace) barrows from a herd known to be free of *A. pleuropneumoniae* and related respiratory pathogens were used. Pigs were housed in the Michigan State University Research Containment Facility and fed a standard antibiotic-free diet provided by the MSU Swine Research and Teaching Center.

Preparation of Vaccines

1. Live vaccine: The bacterial strain used to prepare the live attenuated vaccine was AP233, a derivative of the species type strain, ATCC27088 (here designated APP-1A) that is resistant to nalidixic acid (Nal$^R$), resistant to kanamycin (Kan$^R$), and that requires riboflavin (Rib-) because it contains a riboflavin biosynthetic operon that has been mutated by deletion-disruption with a kanamycin resistance cassette. Bacteria for the live vaccine were grown in heart infusion broth containing 10 µg/ml NAD (nicotine adenine dinucleotide)+5 mM $CaCl_2$+200 µg/ml riboflavin, at 37 C., to an optical density at 520 nm of 0.8. Bacteria were harvested, washed once in phosphate buffered saline (PBS), pH 7.0, diluted in phosphate buffered saline (PBS) or PBS containing 5 µg/ml riboflavin to the appropriate cell density, and used immediately as vaccine.

2. Bacterin: Virulent APP-1A bacteria were grown in heart infusion broth containing 10 µg/ml NAD (nicotine adenine dinucleotide)+5 mM $CaCl_2$ at 37 C., shaking at 160 rpm, to an optical density at 520 nm of 0.8. Bacteria were harvested by centrifugation and washed once with Tris-acetate-EDTA-DTT buffer. Bacteria were resuspended in buffer containing 0.2% formalin to a concentration of $5\times10^9$ cfu/ml, and kept at room temperature for 1 hour, then stored at 4° C. Each vaccine dose contained 1 ml formalinized cells, 0.5 ml saline, and 0.5 ml Emulsigen adjuvant (MVP Laboratories, Ralston, Nebr.).

Vaccine groups. There were six treatment groups (six pigs/group) in this study. Pigs were blocked by starting weight and randomly assigned to treatment groups. The animals were vaccinated twice at a 3 week interval, and challenged with virulent APP serotype 1A (APP-1) two weeks after the second vaccination. Group 1 received $5\times10^8$ cfu (100×the 50% lethal dose previously established for the wild type parent strain [WT $LD_{50}$]) of live AP233, our APP-1 riboflavin-requiring mutant, in 10 ml of sterile PBS, by percutaneous transtracheal inoculation, as in our challenge model (described below). Group 2 received the same treatment as Group 1, except the bacteria were suspended in 10 ml of PBS containing 5 µg/ml riboflavin, a concentration of exogenous riboflavin sufficient to permit 2–3 generations of growth. Group 3 received $5\times10^8$ cfu of live AP233, intramuscularly in 2 ml PBS. Group 4 received the same treatment as Group 3, except the bacteria were suspended in PBS plus 5 µg/ml riboflavin. Group 5 received a formalinized whole cell bacterin prepared from APP-1, which contained the equivalent of $5\times10^9$ cfu per dose, in 2 ml of 25% Emulsigen adjuvant (MVP Laboratories, Ralston, Nebr.). Group 6 were unvaccinated controls.

Experimental challenge. Two weeks after the second vaccination, all groups of pigs were challenged with virulent wild type APP-1A, using an experimental challenge model (Jolie, R. A. V., M. H. Mulks, and B. J. Thacker. 1995. Cross-protection experiments in pigs vaccinated with *Actinobacillus pleuropneumoniae* subtypes 1A and 1B. Vet. Microbiol. 45: 383–391; Thacker, B. J., M. H. Mulks, B. Yamini, & J. Krehbiel. 1988. Clinical, immunological, hematological, microbio-logical, and pathological evaluation of a percutaneous intratracheal injection *Haemophilus pleuropneumoniae* challenge model. Proc. Int. Pig Vet. Soc. 10: 69). For the challenge inoculum, bacteria were grown to late exponential phase in heart infusion broth containing 10 µg/ml NAD 5 mM $CaCl_2$, washed once in sterile saline, and diluted in saline to the appropriate cell density. Pigs were anesthetized by intravenous injection with a mixture of ketamine (6.6 mg/kg) and xylazine (1.65 mg/kg) and inoculated transtracheally with 1 $LD_{50}$ ($5\times10^6$ cfu) of APP-1 suspended in 10 ml saline. Clinical signs, including increased rectal temperature, increased respiration rate, dyspnea, decreased appetite, and depression, were monitored at 4 hour intervals for the first 24 hours post infection, and at 12 hour intervals thereafter. Severely ill animals, as determined by the severity of clinical signs, were euthanized by overdose with a pentobarbital solution (Beuthanasia) delivered intravenously and necropsied immediately. Three days post-infection, all surviving pigs were euthanized and necropsied, and gross pathology of the lungs examined and compared. Lungs were examined macroscopically for APP lesions, including edema, congestion, hemorrhage, infarction, necrosis, abscess, fibrosis, and pleuritis. The percentage of lung tissue and surface area affected was estimated for each of the seven lung lobes, and the data inserted into a formula that weights the contribution of each lung lobe to give a total percentage of lung involvement and affected pleural surface (Thacker, B. J., M. H. Mulks, B. Yamini, & J. Krehbiel. 1988. Clinical, immunological, hematological, microbiological, and pathological evaluation of a percutaneous intratracheal injection *Haemophilus pleuropneumoniae* challenge model. Proc. Int. Pig Vet. Soc. 10: 69). Tissue samples were collected and processed for histopathology, and for culture of APP to confirm infection. Protection of pigs against challenge was measured as a reduction in mortality, in the severity of lung lesions, and in the severity and duration of clinical signs as compared to the unvaccinated control animals. Statistical analysis of the data was conducted using the Statistix microcomputer program (Analytical Software, Tallahassee, Fla.) for analysis of variance (ANOVA) and Epistat (T. L. Gustafson, Round Rock, Tex.) for nonparametric analyses.

Results

Safety. Pigs were monitored post-vaccination for any clinical signs of APP disease, such as fever, dyspnea, and increased respiratory rate, and for injection site reactions in Group 3, 4, and 5 animals. The bacterin vaccinated animals (Group 5) showed mild fever, depression, and decrease in appetite for 8–16 hours post-vaccination, which is a common reaction to bacterin vaccines. Several of the Group 5 animals had granulomatous reactions at the injection site in the neck muscle, which were detected at necropsy. The Group 1 and 2 animals, which received intratracheal immunizations, showed increased respiratory rates, fever, decreased appetite, and mild depression for 8–16 hours post-immunization. The Group 3 and 4 animals, which received the intramuscular vaccine, showed only slight depression and decreased appetite for <8 hours, and no significant fever or increase in respiratory rate. No injection site reactions were detected in the Group 3 or 4 animals at necropsy. These results demonstrate that the live intramuscular vaccine is at least as safe as, if not safer than, a formalinized bacterin of the type routinely used commercially at this time.

Immunogenicity. The immune responses of the pigs to vaccination were evaluated by ELISA against APP outer membranes (Jolie, R. A. V., M. H. Mulks, and B. J. Thacker. 1995. Cross-protection experiments in pigs vaccinated with *Actinobacillus pleuropneumoniae* subtypes 1A and 1B. Vet. Microbiol. 45: 383–391); by hemolysin neutralization titer (Montaraz, J. A., B. Fenwick, H. Hill, and M. Rider. 1996.

Evaluating antibody isotype-specific ELISA, complement fixation, and ApxI hemolysin neutralization tests to detect serum antibodies in pigs infected with *Actinobacillus pleuropneumoniae* serotype 1. Swine Health and Production 4: 79–83); and by complement fixation (CF) (Hoffman, L. J. 1989. *Actinobacillus* (*Haemophilus*) *pleuropneumoniae:* Use of coagglutination and complement fixation to determine the relationship between presence of organisms and antibody titer in slaughterhouse pigs. J. Vet. Diagn. Invest. 1:12–15) (Table 1).

At challenge, the bacterin-vaccinated animals showed significant ELISA and complement fixation titers, but low or negative hemolysin neutralization titers. The four groups receiving live vaccines showed low or negative ELISA and CF titers. However, the Group 3 and 4 animals did show significant hemolysin neutralization titers.

TABLE 6

Serologic analysis of serum samples collected at challenge

| Group # | Vaccine | HN[1] | ELISA-APP1[2] | CF[3] |
|---|---|---|---|---|
| 1 | Live, IT, PBS | $3129 \pm 1478^{b}$ | $227 \pm 90^{b}$ | $1.7 \pm 2.8^{b}$ |
| 2 | Live, IT, PBS + riboflavin | $2520 \pm 741^{b}$ | $164 \pm 73^{b,c}$ | $1.6 \pm 3.1^{b}$ |
| 3 | Live, IM, PBS | $10760 \pm 6245^{a}$ | $120 \pm 32^{b,c}$ | $0.0 \pm 0.0^{b}$ |
| 4 | Live, IM, PBS + riboflavin | $6293 \pm 2662^{a,b}$ | $236 \pm 173^{b}$ | $2.0 \pm 4.0^{b}$ |
| 5 | APP-1A bacterin | $3035 \pm 285^{b}$ | $1119 \pm 170^{a}$ | $24.3 \pm 7.4^{a}$ |
| 6 | Unvaccinated control | $2240 \pm 243^{b}$ | $67 \pm 21^{c}$ | 0.0 ± 0.0b |

[1]Hemolysin neutralization titer; <3000 = negative; 3000–6000 = suspect; >6000 = positive. Assays performed in the laboratory of Dr. Brad Fenwick, Kansas State University.
[2]ELISA vs APP-1 outer membranes; <200 = negative, 200–300 = suspect, >300 = positive. Assays performed in the laboratory of Dr. Martha H. Mulks, Michigan State University.
[3]Complement fixation test; reported as geometric mean titer 0 = negative; >0 = positive. Assays performed at the Veterinary Diagnostic Laboratory, Iowa State University.

Addition of riboflavin to the inoculum. In preliminary studies, it was found that riboflavin-requiring strains of APP failed to persist in the porcine respiratory tract for more than 16–24 hours. Poor persistence of live vaccine strains in vivo can lead to a failure to elicit a protective immune response. *A. pleuropneumoniae* and other related pathogens can produce infection-associated antigens when grown in an appropriate host. These are antigens that are only produced by the bacterium when it is grown within a host animal, presumably due to specific environmental stimuli such as temperature, lack of available iron, pH, or osmotic conditions (Mekalanos, J. J. 1992. Environmental signals controlling expression of virulence determinants in bacteria. Infect. Immun. 174:1–7.). Such infection associated antigens are not produced when the bacterium is grown in vitro in standard laboratory media. In order to assure that such infection-associated antigens would be expressed by the live attenuated vaccine strain of bacteria after immunization of pigs, it was necessary to ensure that the bacteria had sufficient available riboflavin to permit 2–3 generations of growth. It was determined that addition or 5–10 $\mu$g of riboflavin per ml of the vaccine inoculum was sufficient to permit this amount of growth. Therefore, as part of this vaccine trial, intratracheal (IT) and intramuscular (IM) administration of the live attenuated vaccine, with and without the addition of 5 $\mu$g/ml exogenous riboflavin, were compared.

Riboflavin may be added to permit two generations of growth such that the amount may vary from about 1 to about 10 $\mu$g/ml.

Protection against challenge. In this experiment, the live attenuated vaccine prepared with exogenous riboflavin and delivered intramuscularly (Group 4) provided complete protection against mortality (0/5 animals died) and a significant reduction in lung damage and in some clinical signs of pleuropneumonia (Tables 2 and 3). In contrast, 6/6 unvaccinated control animals died From overwhelming pleuropneumonia as a result of this experimental challenge. Other live vaccine formulations, as well as the formalinized bacterin, afforded less protection than the intramuscular immunization containing riboflavin. It is concluded that 1) intramuscular immunization with this live vaccine does elicit significant protection against APP infection; 2) that intratracheal immunization does not elicit the same degree of protection; and 3) that the addition of exogenous riboflavin improves the efficacy of the live vaccine.

Lung cultures. APP was cultured from the lungs of all the challenged pigs except: for 1 animal in Group 4. All cultures were confirmed as APP-LA by gram stain, requirement for NAD, and coagglutination.

TABLE 7

Mortality and Lung Score Data

| Group | Vaccine[1] | Mortality | % Pneumonia[2] | % Pleuritis[3] |
|---|---|---|---|---|
| 1 | Live, IT, PBS | 3/5 | $58.6 \pm 23.5^{a,b}$ | $73.3 \pm 39.3^{a}$ |
| 2 | Live, IT, PBS + riboflavin | 6/6 | $63.2 \pm 8.2^{a,b}$ | $66.7 \pm 51.6^{a}$ |
| 3 | Live, IM, PBS | 4/6 | $57.7 \pm 23.2^{b}$ | $73.3 \pm 42.5^{a}$ |
| 4 | Live, IM, PBS + riboflavin | 0/5 | $24.5 \pm 15.0^{c}$ | $21.5 \pm 20.7^{a}$ |
| 5 | APP-1A bacterin | 3/6 | 54.1 ± 24.8b | $73.9 \pm 41.2^{a}$ |
| 6 | Unvaccinated control | 6/6 | $80.9 \pm 13.2^{a}$ | $83.3 \pm 40.8^{a}$ |

TABLE 7-continued

Mortality and Lung Score Data

| Group | Vaccine[1] | Mortality | % Pneumonia[2] | % Pleuritis[3] |
|---|---|---|---|---|

[1]IT: live vaccine administered by intratracheal inoculation; IM: live vaccine administered by intramuscular injection.
[2]Percentage of lung tissue exhibiting *A. pleuropneumoniae* lesions; results presented as mean ± standard deviation.
[3]Percentage of pleural surface area exhibiting pleuritis; results presented as mean ± standard deviation.
[a···c]Values with different superscripts among the six vaccine groups were significantly different ($p < 0.05$) by Least Significant Difference (LSD) analysis.

TABLE 8

Clinical Score Data

| Group | Vaccine[1] | RR Max[2] | Temp Max[3] | Dyspnea[4] | Depression[5] | Appetite[6] |
|---|---|---|---|---|---|---|
| 1 | Live, IT, PBS | 22.0 ± 5.2[a] | 104.7[a] | 1.80 ± .45[a,b] | 1.40 ± .55[a] | 2.00 ± .71[a] |
| 2 | Live, IT, PBS + riboflavin | 19.7 ± 5.7[a] | 104.0[a] | 2.17 ± .41[a] | 1.67 ± .82[a] | 0.75 ± .96[b,c] |
| 3 | Live, IM, PBS | 19.2 ± 1.2[a] | 104.7[a] | 1.83 ± 41[a,b] | 1.27 ± .75[a] | 2.33 ± 1.21[a] |
| 4 | Live, IM, PBS + riboflavin | 18.2 ± 3.4[a] | 104.2[a] | 1.20 ± .75[b] | 0.40 ± .89[a] | 0.20 ± .45[c] |
| 5 | APP-1A bacterin | 23.3 ± 1.6[a] | 104.7[a] | 1.83 ± 52[a,b] | 1.83 ± .75[a] | 1.67 ± 1.03[a,b] |
| 6 | Unvaccinated control | 23.0 ± 5.8[a] | 104.9[a] | 2.33 ± .52[a] | 1.83 ± .75[a] | 1.83 ± .90[a,b] |
|  | Normal | 8.0 | <103.0 | 0 | 0 | 0 |
|  | Maximum | 25 |  | 3 | 3 | 3 |

[1]IT: live vaccine administered by intratracheal inoculation; IM: live vaccine administered by intramuscular injection.
[2]Maximum respiratory rate observed after challenge. Respiratory rate recorded as number of breaths per 15 second observation period.
[3]Maximum rectal temperature after challenge, in degrees Fahrenheit.
[4]Maximum dyspnea score observed after challenge. Dyspnea score measures degree of respiratory distress and labored breathing. Scored as 0 = normal; 1 = slight; 2 = moderate; 3 = severe.
[5]Maximum depression score observed after challenge. Depression score evaluates attitude and activity. Scored as 0 = normal; 1 = slight inactivity; 2 = moderate; 3 = severe.
[6]Appetite was scored as 0 = did eat; 1 = did not eat. Total score = number of 12 hour periods not eating over 36 hour observation period.
[a···c]Values with different superscripts among the six vaccine groups were significantly different ($p < 0.05$) by Least Significant Difference (LSD) analysis.

It is concluded that intramuscular vaccination with the live attenuated riboflavin-requiring *A. pleuropneumoniae* mutant, with the addition of a limited amount of exogenous riboflavin, led to complete protection against mortality and to significant reduction in lung damage and clinical signs of pleuropneumonia.

The applicants have determined that other related species of pathogenic bacteria in the Family Pasteurellaceae contain homologous genes encoding riboflavin biosynthetic enzymes. Southern blot analysis of genomic DNA from *Actinobacillus suis* and *Pasteurella haemolytica* demonstrated that these species contain DNA fragments that are highly homologous to the rib genes from *A. pleuropneumoniae*. Genomic DNA from these species was digested with the restriction endonucleases EcoRI and HindIII, fragments separated on an agarose gel, and the fragments transferred to nitrocellulose. The nitrocellulose blot was probed with a digoxigenin-labelled probe prepared from the ribGBAH operon from APP serotype 5, at 42° C., in a hybridization cocktail that included 50% formamide, 5×SSC (20×SSC contains 3 M NaCl and 0.3 M sodium citrate, pH 7. 0), 0.1% N-lauroylsarcosine, and 0.02% SDS. The blot was washed under high stringency conditions, including two 15 minute washes at room temperature in 2×SSC, 0.1% SDS, followed by two 30 minute washes at 68° C. in 0.1×SSC, 0.1% SDS. *P.haemolytica* contains an ~12 kb DNA HindIII fragment that hybridized with the rib probe, while *A. suis* contains three EcoRI fragments of ~4.4, 2.5, and 1.0 kb that are highly homologous to the APP-5 rib probe. These data suggest that these species of bacteria contain riboflavin operons that are similar to that analyzed from APP serotype 5.

A live avirulent vaccine against APP is desirable. There are a variety of different kinds of vaccines produced to elicit protection against bacterial diseases. Some of the most effective are purified toxins converted to toxoids. These toxoid vaccines are often very safe, and can be very effective against diseases where a toxin is the major virulence factor. Examples would be current vaccines against tetanus and diphtheria. These vaccines do not prevent acquisition and carriage of the causative organism, e.g, *Clostridium tetani*, the causative agent of tetanus, or *Corynebacterium diphtheriae*, the agent of diphtheria. Rather, they prevent the deleterious effects of the toxin by eliciting antibodies that neutralize the toxin. n other cases where a key virulence factor has been identified, purified protein or polysaccharide vaccines have been produced. Examples here would be the *E. coli* pilin vaccine against porcine colibacillosis and the capsular polysaccharide vaccines now available against *Haemophilus influenzae* B, *Streptococcus pneumoniae*, and some serotypes of *Neisseria meningitidis*. These vaccines either prevent initial adherence of the pathogen, as in the case of the pilin vaccine, or enhance phagocytosis and clearance of the pathogen, as in the case of the pilin vaccine, or enhance In the veterinary field, it is also common to use bacterin vaccines, that is, killed whole cell vaccines. Because these bacterins can induce a wide range of side effects, they are not commonly used for human vaccines. A problem with all of these types of vaccines is that they generally induce systemic humoral immunity, i.e., serum antibodies. It is difficult to induce local secretory immunity with these types of vaccines. Live avirulent vaccines, where the recipient of the vaccine receives a dose of infectious but not virulent bacteria, can be an improvement over purified subunit or killed whole cell vaccines, for several reasons. First, the vaccine dose can often be administered to the same region of the body that is normally infected by the pathogen, e.g., orally for a gastrointestinal pathogen or as a nasal spray for a respiratory pathogen. This can elicit local secretory immunity as well as systemic humoral immunity. Second, live avirulent vaccines can often be administered as a single dose rather than multiple doses, because the organism can continue to grow and replicate within the host, providing a longer term exposure to important antigens that a single dose of killed vaccine. Finally, live avirulent vaccines may provide exposure to important bacterial antigens not contained in killed vaccines grown in the laboratory. For example, if a bacterium produces important antigens or virulence actors whose expression is induced by in vivo environmental signals, these antigens may not be contained in a vaccine prepared from bacteria grown in vitro in laboratory media. It is desirable for a vaccine to elicit cross-protective immunity against the different serotypes of APP. It is known that vaccination with a killed whole cell vaccine prepared from a single serotype of APP will usually not elicit cross-protective immunity against other serotypes. However, infection with a virulent strain of APP will generally elicit at least some degree of cross-protection against other serotypes. One explanation for this phenomenon is that antigens may be expressed by APP during growth in vivo that elicit a cross-protective immune response, and that these antigens are not contained in most bacteria vaccines.

Specifically, it has been shown that extracellular toxins, referred to as hemolysins/cytolysins, are produced by APP in vivo but are not produced under the culture conditions typically used for producing killed whole cell vaccines.

The applicants have shown that riboflavin-requiring mutants of APP can be effective as a live avirulent vaccine. There are two basic methods or producing live avirulent vaccine strains. One is to knock out a critical virulence factor necessary for survival in vivo and perhaps also for disease/damage to the host. An example would be Inzana's non-capsulated APP mutants. These mutants are unable to synthesize capsular polysaccharide, which acts in vivo to protect the bacterium from phacocytosis and clearance by alveolar macrophages. Non-capsulated mutants simply can not survive long enough in vivo to cause disease. They do, however, presumably express all the other important virulence factors and therefore should elicit an immune response against antigens other than capsular polysaccharide.

A second method to produce live avirulent vaccines is to knock out genes in biosynthetic pathways known to be critical for survival in vivo. For example, the availability of compounds such as purines and aromatic amino acids is limited in mammalian hosts. Bacterial pathogens must be able to synthesize these compound themselves, or scavenge them from host tissues. Mutations in the biosynthetic pathways for purines and aromatic amino acids have been used to construct bacterial mutants that can not survive long in vivo, and thus have potential for use as attenuated vaccines. Much of the current research on genetically engineered live avirulent vaccines has been done with members of the genus Salmonella. These studies show that purA mutants are avirulent but poorly immunogenic (O'Callaghan et al, 1988), while mutations in the chorismate pathway, including aroA, aroC, and aroD, are attenuated and can be effective as live oral vaccines (Doggett & Curtiss, 1992; Tacket et al, 1992). In addition, Salmonella strains carrying cya and crp mutations, which produce mutants that lack the enzyme adenylate cyclase and the cyclic AMP receptor protein, which are required for the expression of numerous critical genes in bacteria, have been shown to be both avirulent and immunogenic (Doggett & Curtiss, 1992; Tacket et al, 1992; Kelly et al, 1992).

Riboflavin is an essential vitamin and biosynthetic precursor for the coenzymes FMN and FAD. It is synthesized by most bacteria, but not by mammals. Therefore, it is expected that riboflavin would be in limited supply in a mammalian host and that a bacterium incapable of synthesizing its own riboflavin would be attenuated. This has been shown above. It has also been shown above that Rib-mutants can survive long enough in the host to be immunogenic and effective as a live avirulent vaccine.

The rib-APP mutant may be combined with a sterile, buffered, isotonic, pharmaceutically-acceptable and compatible aqueous carrier such as saline, or saline derivative such as citrate-buffered saline, tris-buffered saline, Ringer's Solution or tissue culture medium, and the like, preferably having a physiologic pH. An antigen composition may also include a suitable compatible adjuvant such as aluminum hydroxide, paraffin-based oils, averdine, muramyl dipeptide, and the like, to stabilize the antigen in solution, and/or an immunomodulator such as a recombinant cytokine or interleukin such as IL-1, IL-5, IL-6, TGF-beta, or gamma interferon, and the like, to enhance the IgA antibody response. However, the adjuvant chosen should not contain any preservative, such as formalin, that would be deleterious to a live vaccine. In the experiments described above, no adjuvant was used.

The vaccine composition may be formulated for administration as a single injection of about 0.5 to 10 ml. The composition may also be in the form for administration in a series of biweekly or monthly injections of about 0.5 to 10 ml each, until the desired level of immunity is achieved. Preferably, the composition is formulated for a single administration to the animal.

The vaccine composition as described herein may be formulated with conventional pharmaceutically acceptable vehicles for administration by transthoracic intrapulmonary injection, intratracheal innoculation, subcutaneous, intraperitoneal or intramuscular injection. The vaccine may also be supplied orally or intranasally. These vehicles comprise substances that are essentially nontoxic and nontherapeutic such as saline and derivatives of saline such as citrate-buffered saline, tris-buffered saline and Ringer's Solution, dextrose solution, Hank's Solution, tissue culture medium, and the like. The antigen composition may also include minor but effective amounts of pharmaceutically-accepted adjuvants, buffers and preservatives to maintain isotonicity, physiological pH, and stability. Adjuvants useful in the composition include, but are not limited to, for example, paraffin based oils, averdine, muramyl dipeptide, and oil-in-water-based adjuvants, and the like. Examples of suitable buffers include but not limited to, phosphate buffers, citrate buffers, carbonate buffers, TRIS buffers, and the like. It is also envisioned that the antigen may be combined with a biocompatible, and optimally synergistic, immunomodulator that cooperatively stimulates IgA antibody production, as for example, but not limited to, recombinant cytokines such as TGF-beta, interferons, activating factors, chemoattractants, interleukins such as IL-1, IL-2, IL-4, IL-5, IL-6 and the like, and other like substances.

While the forms of the invention herein disclosed constitute presently preferred embodiments, many others are possible. It is not intended here to mention all the possible equivalent forms or ramifications of the invention. It is understood that the terms used herein are merely descriptive, and that various changes may be made without departing from the spirit or scope of the invention.

REFERENCES

1. Bacher, A. 1991. Biosynthesis of flavins, p. 215–259. In F. Muller (ed.), Chemistry and Biochemistry of Flavins, vol. 1. Chemical Rubber Co., Boca Raton, Fla.
2. Bandrin, S. V., P. M. Rabinovich, and A. I. Stepanov. 1983. Three linkage groups of genes involved in riboflavin biosynthesis in *Escherichia coli*. Sov. Genet. 19:1103–1109.
3. Bresler, S. E., E. I. Cherepenko, T. P. Chernik, V. L. Kalinin, and D. A. Perumov. 1970. Investigation of the operon of riboflavin synthesis in *Bacillus subtilis*. I. Genetic mapping of the linkage group. Genetika 6:116–124.
4. Bresler, S. E., E. A. Glazunov, G. I. Chernik, T. N. Shevchenko, and D. A. Perumov. 1973. Investigation of the operon of riboflavin synthesis in *Bacillus subtilis*. V. Flavin mononucleotide and flavin adenine dinucleotide as effectors in the operon of riboflavin biosynthesis. Genetika 9:84–91.
5. Bresler, S. E., V. L. Kalinin, A. S. Kriviskii. D. A. Perumov. and T. P. Chernik. 1969. Mutant of *Bacillus subtilis* synthesizing notable amounts of riboflavin. Genetika 5:133–138.
6. Bresler, S. E., D. A. Perumov, G. I. Chernik, A. P. Skvortsova. 1976. Investigation of the operon of riboflavin synthesis in *Bacillus subtilis*. XI. Determination of the type of regulation by a test for dominance of operator-constitutive and regulator-constitutive mutations. Genetika 12:124–130.
7. Chikindas, M. L., G. I. Morozov, V. N. Mironov, E. V. Luk'yanov, V. V. Emel'yanov, and A. I. Stepanov. 1988. Regulatory regions of the riboflavin operon in *Bacillus subtilis*. Dokl. Akad. Nauk SSSR 298:997–1000.
8. Christen, A. A., M. L. Pall, T. Manzara and P. F. Lurquin. 1983. Rapid isolation of *Escherichia coli* minicells by glass-fiber filtration: study of plasmid-coded polypeptides. Gene 23:195–198.
9. Fenwick, B. and Henry, S. 1994. Porcine pleuropneumonia. J. Am. Vet. Med. Assoc. 204:1334–1340.
10. Foster, E. W., D. C. Gyure, D. L. Heefner, C. A. Weaver, M. J. Yarus, L. A. Burdzinski. June 1992. U.S. Pat. No. 5,120,655.
11. Genetics Computer Group. September 1994. Program Manual for the Wisconsin Package, Ver. 8. Genetics Computer Group. Madison, Wis.
12. Hawley, D. K. and W. R. McClure. 1983. Compilation and analysis of *Escherichia coli* promoter DNA sequences. Nucleic Acids. Res. 11:2237–2255.
13. Holmes, W. M., T. Platt, and M. Rosenber. 1983. Termination of transcription in *E. coli*. Cell 32:1029–1032.
14. Hunneman, W. A. 1986. Incidence, economic effects, and control of *Haemophilus pleuropneumoniae* infections in pigs. Vet. Quarterly 8:83–87.
15. Inzana, T. J., J. Todd, and H. P. Veit. 1993. Safety, stability and efficacy of nonencapsulated mutants of *Actinobacillus pleuropneumoniae* for use in live vaccines. Infect. Immun. 61:1682–1686.
16. Lee, C. Y., D. J. O'Kane, and E. A. Meighen. 1994. Riboflavin synthesis genes are linked with the lux operon of *Photobacterium phosphoreum*. J. Bacteriol. 176:2100–2104.
17. Lee, C. Y. and E. A. Meighen. 1992. The lux genes in *Photobacterium leiognathi* are closely linked with genes corresponding in sequence to riboflavin synthesis genes. Biochem. Biophys. Res. Commun. 186:690–697.
18. Mironov, V. N., M. L. Chikindas. A. S. Kraev, A. I. Stepanov. and K. G. Skryabin. 1990. Operon organization of genes of riboflavin biosynthesis in *Bacillus subtilis*. Dok. Akad. Nauk SSSR 312:237–240.
19. Mironov, V. N., A. S. Kraev, B. K. Chernov, A. V. Ul'yanov. Y. B. Golva, G. E. Pozmogova, M. L. Simonova, V. K. Gordeev, A. I. Stepanov, and K. G. Skryabin. 1989. Genes of riboflavin biosynthesis of *Bacillus subtilis*-complete primary structure and model of organization. Dokl. Akad. Nauk SSSR 305:482–487.
20. Mironov, V. N., D. A. Perumov, A. S. Kraev, A. I. Stepanov, K. G. Skryabin. 1990. Unusual structure in the regulation region of the *Bacillus subtilis* riboflavin biosynthesis operon. Molekulyarnaya Biologiya 24:256–261.
21. Morse, S. A. and L. Bartenstein. 1980. Purine metabolism in *Neisseria gonorrhoeae:* the requirement for hypoxanthine. Can. J. Microbiol. 26:13–20.
22. Needleman, S. B. and C. D. Wunsch. 1970. A general method applicable to the search for similarities in the amino acid sequence of two proteins. J. Molec. Biol. 48:443–453.
23. Nicolet, J. 1992. *Actinobacillus pleuropneumoniae*, p. 401–408. In A. D. Leman et al (eds), Diseases of Swine, 7th edition. Iowa State University Press, Ames, Iowa.
24. Nielsen, R. 1979. *Haemophilus parahaemolyticus* serotypes: pathogenicity and cross immunity. Nord. Vet. Med. 31:407–413.
25. Nielsen, R. 1984. *Haemophilus pleuropneumoniae* serotypes—Cross protection experiments. Nord. Vet. Med. 36:221–234.
26. Nielsen, R. 1976. Pleuropneumonia of swine caused by *Haemophilus pleuropneumoniae*. Studies on the protection obtained by vaccination. Nord. Vet. Med. 28:337–338.
27. Nielsen, R. 1974. Serological and immunological studies of pleuropneumonia of swine caused by *Haemophilus parahaemolyticus*. Acta Vet. Scand. 15:80–89.
28. Paltineanu, D., R. Pambucol, E. Tirziu, and I. Scobercea. 1992. Swine infectious pleuropneumonia: Aerosol vaccination with a live attenuated vaccine. Proc. Int. Pig. Vet. Soc. 12:214.
29. Perkins, J. B., and J. G. Pero. 1993. Biosynthesis of riboflavin, biotin, folio acid, and cobalamin, p. 319–334. In A. Sonenshein (ed.), *Bacillus subtilis* and other gram-positive bacteria: biochemistry, physiology, and molecular genetics. American Society for Microbiology. Washington, D.C.
30. Perkins, J. B., J. G. Pero, and A. Sloma. January 1991. Riboflavin overproducing strains of bacteria. European patent application 0405370.
31. Perry, M. B., E. Altman, J.-R. Brisson, L. M. Beynon, and J. C. Richards. 1990. Structural characteristics of the antigenic capsular polysaccharides and lipopolysaccharides involved in the serological classification of *Actinobacillus pleuropneumoniae* strains. Serodiag. Immunother. Infect. Dis. 4:299:308.
32. Reeve, J. 1977. Bacteriophage infection of minicells: a general method for identification of in vivo bacteriophage directed polypeptide biosynthesis. Molec. Gen. Genet. 158:73–79.

33. Richter, G., H.33. Ritz, G. Katzenmeier, R. Volk, A. Kohnle, F. Lottspeich, D. Allendorf, and A. Bacher. 1993. Biosynthesis of riboflavin: Cloning, sequencing, mapping and expression of the gene coding for GTP cyclohydrolase II in *Escherichia coli*. J. Bacteriol. 175:4045–4051.
34. Richter, G., R. Volk, C. Krieger, H. W. Lahm, U. Rothlisberger, and A. Bacher. 1992. Biosynthesis of riboflavin: cloning sequencing, and expression of the gene coding 3,4-dihydroxy-2 -butanone 4-phosphate synthase of *Escherichia coli*. J. Bacteriol. 174:4050–4056.
35. Rosendal, S., D. S. Carpenter, W. R. Mitchell, and M. R. Wilson. 1981. Vaccination against pleuropneumonia in pigs caused by *Haemophilus pleuropneumoniae*. Can. Vet. J. 22:34–35.
36. Sambrook, J., E. F. Fritsch, and T. Maniatis. 1989. Molecular Cloning: A Laboratory Manual, 2nd. ed. Cold Spring Harbor Press, Cold Spring Harbor, N.Y.
37. Sanger, F., S. Milken, and A. R. Coulson. 1977. DNA sequencing with chain-terminating inhibitors. Proc. Natl. Acad. Sci. 74:5463–5467.
38. Schott, K., J. Kellermann, F. Lottspeich, and A. Bacher. 1990. Riboflavin synthases of *Bacillus subtilis*: purification and amino acid sequence of the α-subunit. J. Biol. Chem. 265:4204–4209.
39. Sebunya, T. N. K., and J. R. Saunders. 1983. *Haemophilus pleuropneumoniae* infection in swine: A review. J. Amer. Vet. Med. Asscoc. 182:1331–1337.
40. Shavlovskii, G. M., and E. M. Logvinenko. 1988. Flavin oversynthesis in microorganisms and its molecular mechanisms (review). Prikladnaya Biokhimiya i Mikrobiologiya 24:435–447.
41. Swartzman, E., C. Miyamoto, A. Graham, and E. A. Meighen. 1990. Delineation of the transcriptional boundaries of the lux operon of *Vibrio harveyi* demonstrates the presence of two new lux. genes. J. Biol. Chem. 265:3513–3517.
42. Tetsuya, T., C. Ueguchi, K. Shiba., and K. Ito. 1992. Insertional disruption of the nusB (ssyB) gene leads to cold-sensitive growth of *Escherichia coli* and suppression of the secY24 mutation. Mol. Gen. Genet. 234:429–432.
43. Thacker, B. J., and M. H. Mulks. 1988. Evaluation of commercial *Haemophilus pleuropneumoniae* vaccines. Proc. int. Pig Vet. Soc. 10:87.
44. Utrera, V., C. Pijoan, and T. Molitor. 1992. Evaluation of the immunity induced in pigs after infection with a low virulence strain of *A. pleuropneumoniae* serotype 1. Proc. Int. Pig Vet. Soc. 12:213.
45. Vieira, J. and J. Messing. 1982. The pUC plasmids, an M13mp7-derived system for insertion mutagenesis and sequencing with synthetic universal primers. Gene 19:259–268.
46. Wilson, A. C. and A. B. Pardee. 1962. Regulation of flavin synthesis by *Escherichia coli*. J. Gen. Microbiol. 28:283–303.
47. Doggett, T. A., & R. Curtiss III. 1992. Delivery of antigens by recombinant avirulent and Salmonella strains. In J. E. Ciardi et al, Genetically Engineered Vaccines, Plenum Press, New York, pp.165–173.
48. Kelly, S. M., B. A. Bosecker, & R. Curtiss III. 1992. Characterization and protective properties of attenuated mutants of *Salmonella choleraesuis*. Infect. Immun. 60: 4881–4890.
49. O'Callaghan, D., et al. 1988. Characterization of aromatic and purine-dependent *Salmonella typhimurium*: attenuation, persistence, and ability to induce protective immunity in Balb/c mice . Infect. Immun. 56: 419–423.
50. Tacket, C. O., et al. 1992. Comparison of the safety and immunogenicity of ΔaroC ΔaroD and Δcya Δcrp *Salmonella typhi* strains in adult volunteers. Infect. Immun. 60: 536–541.

What is claimed is:

1. A live vaccine against members of the family of Pasteurellaceae comprising a recombinant mutant of a member of the family of Pasteurellaceae lacking a rib gene necessary for the production of riboflavin in a pharmaceutically acceptable carrier.

2. The vaccine of claim 1 wherein said members of the family of Pasteurellaceae are selected from the group consisting of *Pasteurella multocida, Pasteurella haemolytica, Actinobacillus suis, Haemophilus parasuis, Haemophilus influenzae,* and *Haemophilus ducreyi.*

3. The vaccine of claim 1 wherein said rib gene is selected from the group consisting of rib G, rib A, rib B, and rib H.

4. A method of vaccinating a mammal in need thereof comprising administering to the mammal an effective vaccinating amount of a live vaccine comprising a recombinant mutant of a member of the family of Pasteurellaceae lacking a rib gene necessary for the production of riboflavin in a pharmaceutically acceptable carrier.

5. A method of stimulating the immune system of a mammal in need thereof comprising the steps of:
   (a) providing a recombinant Pasteurellaceae mutant having an inactivating mutation in one or more rib genes necessary for the production of riboflavin; and
   (b) administering an effective immunogenic amount of the recombinant Pasteurellaceae mutant in a pharmaceutically acceptable carrier to a mammal in need thereof, thereby causing an antigenic response thereto, which stimulates the immune system in the mammal.

6. A method of inducing protective immunity in a mammal in need thereof against disease caused by Family Pasteurellaceae comprising the step of administering to the mammal an effective amount of a recombinant Pasteurellaceae mutant having an inactivating mutation in one or more rib genes necessary for the production of riboflavin in a pharmaceutically acceptable carrier such that the mutant causes protective immunity in the mammal against Pasteurellaceae.

7. The vaccine of claim 1 wherein the pharmaceutically acceptable carrier further comprises riboflavin.

8. The method of claim 4 wherein the pharmaceutically acceptable carrier further comprises riboflavin.

9. The method of claim 5 wherein the pharmaceutically acceptable carrier further comprises riboflavin.

10. The method of claim 5 or 6 wherein the rib genes are selected from the group consisting of rib G, rib A, rib B, and rib H.

11. The method of claim 4 wherein said rib gene is selected from the group consisting of rib G, rib A, rib B, and rib H.

* * * * *

UNITED STATES PATENT AND TRADEMARK OFFICE
CERTIFICATE OF CORRECTION

PATENT NO. : 6,410,021 B1
DATED : June 25, 2002
INVENTOR(S) : Troy E. Fuller, Martha H. Mulks and Bradley Thacker It is certified that error appears in the above-identified patent and that said Letters Patent is hereby corrected as shown below:

Title page,
Insert Item [73] as follows: -- [73] Assignees: Michigan State University, East Lansing, Michigan; and Iowa State University Research Foundation, Inc., Ames Iowa --

Column 2,
Line 2, "nutagenesis" should be -- mutagenesis --.

Column 3,
Line 25, "gale derivatives" should be -- *galE* derivatives --.

Column 4,
Line 1, "Quantities" should be -- quantities --.

Column 5,
Line 41, "shows" after "show" and before "the" should be deleted.

Column 6,
Line 55, "nay be" should be -- may be --.

Column 7,
Line 55, "(BSV3) mutants" should be -- (BSV13) mutants --.
Line 64, "according Lo" should be -- according to --.

Column 8,
Line 28, "(5'GGC-C-AC-ACG" should be -- (5'-GGC-GAC-ACG --.

Column 12,
Table 2, line 47, (in the heading), "either wide" should be -- either wild --.

Column 14,
Line 25, "APP225 and APP33" should be -- AP225 and AP233 --.
Line 32, "Laemnli" should be -- Laemmli --.
Line 56, "calorimetric" should be -- colorimetric --.

Column 17,
Table 3, line 62, "(λ801acZΔ" should be -- (Φ801acZΔ --.

UNITED STATES PATENT AND TRADEMARK OFFICE
CERTIFICATE OF CORRECTION

PATENT NO. : 6,410,021 B1
DATED : June 25, 2002
INVENTOR(S) : Troy E. Fuller, Martha H. Mulks and Bradley Thacker It is certified that error appears in the above-identified patent and that said Letters Patent is hereby corrected as shown below:

Column 18,
Table 3, line 33, "AP106 ribGBAH" should be -- AP106 *ribBAH* --.
Table 4, line 63, "wild-type APP 225-serotype" should be -- wild type AP 225-serotype --.

Column 19,
Table 5, line 13, "APP225-serotype" should be -- AP225-serotype --.
Line 30, "ribGBAH operon" should be -- *ribBAH* operon --.

Column 21,
Line 22, "APP-LA bacteria" should be -- APP-1A bacteria --.

Column 24,
Line 3, "addition or" should be -- addition of --.
Line 37, "From overwhelming" should be -- from overwhelming --.
Line 49, "except: for 1 animal" should be -- except for 1 animal --.
Line 51, "APP-LA" should be -- APP-1A --.

Column 26,
Line 54, "toxin. n other" should be -- toxin. In other --.
Lines 63-64, "case of the pilin vaccine, or enhance In the" should be -- case of the capsular polysaccharide vaccines. In the vet --.

Column 27,
Line 16, "that a" should be -- than a --.
Line 19, "virulence actors" should be -- virulence factors --.
Line 47, "phacocytosis" should be -- phagocytosis --.

Signed and Sealed this

Twenty-fifth Day of March, 2003

JAMES E. ROGAN
*Director of the United States Patent and Trademark Office*

SEQUENCE LISTING

```
<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer for DNA sequencing rib
      genes

<400> SEQUENCE: 1
aatccggcaa aaattgaagg c                                              21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer for DNA sequencing rib
      genes

<400> SEQUENCE: 2
gcaccgtgac gcactaacg                                                 19
```

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer for DNA sequencing rib
      genes

<400> SEQUENCE: 3
gcgccaatac ttgctcaccg                                                 20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer for DNA sequencing rib
      genes

<400> SEQUENCE: 4 ggtttctttta ttcgtatgcg g                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer for DNA sequencing rib
      genes

<400> SEQUENCE: 5
tgaagaagtc ggcaaattgc t                                               21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer for DNA sequencing rib
      genes

<400> SEQUENCE: 6
cggattggga ttcgtccagc c                                               21

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer for DNA sequencing rib
      genes

<400> SEQUENCE: 7
ggcgacacga ttgcggtg                                                   18

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer for DNA sequencing rib
      genes
```

-continued

```
<400> SEQUENCE: 8
gccagttagt gcagacagcg                                                      20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer for DNA sequencing rib
      genes

<400> SEQUENCE: 9
ctcaccggtt cctgccaaac c                                                    21

<210> SEQ ID NO 10
<211> LENGTH: 1203
<212> TYPE: DNA
<213> ORGANISM: Actinobacillus pleuropneumoniae
<220> FEATURE:
<221> NAME/KEY: CDS
<222> LOCATION: (1)..(1203)
<223> OTHER INFORMATION: rib A

<400> SEQUENCE: 10 atg aca gat ttc caa ttt tca aaa gta gaa gat gcg atc gaa gcg att            48
Met Thr Asp Phe Gln Phe Ser Lys Val Glu Asp Ala Ile Glu Ala Ile
  1               5                  10                  15 cga caa ggc aaa atc att tta gtg act gac gat gaa gat cgc gaa aac            96
Arg Gln Gly Lys Ile Ile Leu Val Thr Asp Asp Glu Asp Arg Glu Asn
             20                  25                  30 gaa ggc gat ttt atc tgt gcg gcg gaa ttt gcc aca ccg gaa aat atc           144
Glu Gly Asp Phe Ile Cys Ala Ala Glu Phe Ala Thr Pro Glu Asn Ile
         35                  40                  45 aat ttt atg gca act tac ggc aaa ggt ttg att tgt acg ccg att tca           192
Asn Phe Met Ala Thr Tyr Gly Lys Gly Leu Ile Cys Thr Pro Ile Ser
     50                  55                  60 acc gaa atc gct aaa aaa tta aat ttc cat ccg atg gtt gcg gtc aat           240
Thr Glu Ile Ala Lys Lys Leu Asn Phe His Pro Met Val Ala Val Asn
 65                  70                  75                  80 caa gat aat cat gaa acg gcg ttt acc gta tcg gtg gat cat att gat           288
Gln Asp Asn His Glu Thr Ala Phe Thr Val Ser Val Asp His Ile Asp
                 85                  90                  95 acg gga acg ggt atc tca gct ttt gag cgt tcg att acc gca atg aaa           336
Thr Gly Thr Gly Ile Ser Ala Phe Glu Arg Ser Ile Thr Ala Met Lys
            100                 105                 110 att gtc gat gat aat gct aaa gca acg gat ttc cgc cgc ccg ggg cat           384
Ile Val Asp Asp Asn Ala Lys Ala Thr Asp Phe Arg Arg Pro Gly His
        115                 120                 125 atg ttt ccg tta atc gct aaa gaa ggt gga gtg tta gtg cgt aac ggt           432
Met Phe Pro Leu Ile Ala Lys Glu Gly Gly Val Leu Val Arg Asn Gly
    130                 135                 140 cat acc gaa gca aca gtg gat tta gct cgt tta gcc ggt tta aaa cac           480
His Thr Glu Ala Thr Val Asp Leu Ala Arg Leu Ala Gly Leu Lys His
145                 150                 155                 160 gcc ggt tta tgt tgt gaa att atg gcg gat gac ggc acg atg atg act           528
Ala Gly Leu Cys Cys Glu Ile Met Ala Asp Asp Gly Thr Met Met Thr
                165                 170                 175 atg ccg gat cta caa aaa ttt gcg gta gaa cac aat atg ccg ttt atc           576
Met Pro Asp Leu Gln Lys Phe Ala Val Glu His Asn Met Pro Phe Ile
            180                 185                 190 acg att caa caa tta caa gaa tat cgc cgt aag cat gac agc ttg gtg           624
```

-continued

```
Thr Ile Gln Gln Leu Gln Glu Tyr Arg Arg Lys His Asp Ser Leu Val
            195                 200                 205 aaa caa att tct gtg gta aaa atg ccg aca aaa tac ggt gag ttt atg       672
Lys Gln Ile Ser Val Val Lys Met Pro Thr Lys Tyr Gly Glu Phe Met
        210                 215                 220 gca cat agc ttt gtt gaa gtg att tca ggt aaa gaa cac gtt gcg tta       720
Ala His Ser Phe Val Glu Val Ile Ser Gly Lys Glu His Val Ala Leu
225                 230                 235                 240 gtc aaa ggc gat tta acc gac ggt gag caa gta ttg gcg cgt atc cat       768
Val Lys Gly Asp Leu Thr Asp Gly Glu Gln Val Leu Ala Arg Ile His
                245                 250                 255 tcg gaa tgt tta acc ggt gac gct ttc ggt tct caa cgt tgt gat tgc       816
Ser Glu Cys Leu Thr Gly Asp Ala Phe Gly Ser Gln Arg Cys Asp Cys
            260                 265                 270 ggt cag caa ttt gcc gca gca atg acc caa att gag caa gag ggc aga       864
Gly Gln Gln Phe Ala Ala Ala Met Thr Gln Ile Glu Gln Glu Gly Arg
        275                 280                 285 ggt gtg att ctg tat tta cgc caa gaa ggt cgt ggt atc ggt tta atc       912
Gly Val Ile Leu Tyr Leu Arg Gln Glu Gly Arg Gly Ile Gly Leu Ile
290                 295                 300 aat aag cta cgt gct tac gaa cta caa gat aaa ggg atg gat acc gtt       960
Asn Lys Leu Arg Ala Tyr Glu Leu Gln Asp Lys Gly Met Asp Thr Val
305                 310                 315                 320 gaa gcg aac gtc gct tta gga ttt aaa gaa gac gaa cgt gag tac tat      1008
Glu Ala Asn Val Ala Leu Gly Phe Lys Glu Asp Glu Arg Glu Tyr Tyr
                325                 330                 335 atc ggt gca caa atg ttc cag cag tta ggc gta aaa tcg atc cgt tta      1056
Ile Gly Ala Gln Met Phe Gln Gln Leu Gly Val Lys Ser Ile Arg Leu
            340                 345                 350 tta acc aat aat ccg gca aaa att gaa ggc tta aaa gag caa gga tta      1104
Leu Thr Asn Asn Pro Ala Lys Ile Glu Gly Leu Lys Glu Gln Gly Leu
        355                 360                 365 aat atc gtt gca cgt gag ccg att att gta gaa ccg aac aaa aat gac      1152
Asn Ile Val Ala Arg Glu Pro Ile Ile Val Glu Pro Asn Lys Asn Asp
370                 375                 380 att gat tac cta aaa gtc aaa cag ata aaa atg ggg cat atg ttt aac      1200
Ile Asp Tyr Leu Lys Val Lys Gln Ile Lys Met Gly His Met Phe Asn
385                 390                 395                 400 ttc                                                                    1203
Phe

<210> SEQ ID NO 11
<211> LENGTH: 401
<212> TYPE: PRT
<213> ORGANISM: Actinobacillus pleuropneumoniae

<400> SEQUENCE: 11

Met Thr Asp Phe Gln Phe Ser Lys Val Glu Asp Ala Ile Glu Ala Ile
1               5                   10                  15

Arg Gln Gly Lys Ile Ile Leu Val Thr Asp Asp Glu Asp Arg Glu Asn
            20                  25                  30

Glu Gly Asp Phe Ile Cys Ala Ala Glu Phe Ala Thr Pro Glu Asn Ile
        35                  40                  45

Asn Phe Met Ala Thr Tyr Gly Lys Gly Leu Ile Cys Thr Pro Ile Ser
    50                  55                  60

Thr Glu Ile Ala Lys Lys Leu Asn Phe His Pro Met Val Ala Val Asn
65                  70                  75                  80

Gln Asp Asn His Glu Thr Ala Phe Thr Val Ser Val Asp His Ile Asp
                85                  90                  95
```

```
Thr Gly Thr Gly Ile Ser Ala Phe Glu Arg Ser Ile Thr Ala Met Lys
            100                 105                 110
Ile Val Asp Asp Asn Ala Lys Ala Thr Asp Phe Arg Arg Pro Gly His
        115                 120                 125
Met Phe Pro Leu Ile Ala Lys Glu Gly Val Leu Val Arg Asn Gly
    130                 135                 140
His Thr Glu Ala Thr Val Asp Leu Ala Arg Leu Ala Gly Leu Lys His
145                 150                 155                 160
Ala Gly Leu Cys Cys Glu Ile Met Ala Asp Asp Gly Thr Met Met Thr
                165                 170                 175
Met Pro Asp Leu Gln Lys Phe Ala Val Glu His Asn Met Pro Phe Ile
            180                 185                 190
Thr Ile Gln Gln Leu Gln Glu Tyr Arg Arg Lys His Asp Ser Leu Val
        195                 200                 205
Lys Gln Ile Ser Val Val Lys Met Pro Thr Lys Tyr Gly Glu Phe Met
    210                 215                 220
Ala His Ser Phe Val Glu Val Ile Ser Gly Lys Glu His Val Ala Leu
225                 230                 235                 240
Val Lys Gly Asp Leu Thr Asp Gly Glu Gln Val Leu Ala Arg Ile His
                245                 250                 255
Ser Glu Cys Leu Thr Gly Asp Ala Phe Gly Ser Gln Arg Cys Asp Cys
            260                 265                 270
Gly Gln Gln Phe Ala Ala Ala Met Thr Gln Ile Glu Gln Glu Gly Arg
        275                 280                 285
Gly Val Ile Leu Tyr Leu Arg Gln Glu Gly Arg Gly Ile Gly Leu Ile
    290                 295                 300
Asn Lys Leu Arg Ala Tyr Glu Leu Gln Asp Lys Gly Met Asp Thr Val
305                 310                 315                 320
Glu Ala Asn Val Ala Leu Gly Phe Lys Glu Asp Glu Arg Glu Tyr Tyr
                325                 330                 335
Ile Gly Ala Gln Met Phe Gln Gln Leu Gly Val Lys Ser Ile Arg Leu
            340                 345                 350
Leu Thr Asn Asn Pro Ala Lys Ile Glu Gly Leu Lys Glu Gln Gly Leu
        355                 360                 365
Asn Ile Val Ala Arg Glu Pro Ile Ile Val Glu Pro Asn Lys Asn Asp
    370                 375                 380
Ile Asp Tyr Leu Lys Val Lys Gln Ile Lys Met Gly His Met Phe Asn
385                 390                 395                 400
Phe

<210> SEQ ID NO 12
<211> LENGTH: 645
<212> TYPE: DNA
<213> ORGANISM: Actinobacillus pleuropneumoniae
<220> FEATURE:
<221> NAME/KEY: CDS
<222> LOCATION: (1)..(645)
<223> OTHER INFORMATION: rib B

<400> SEQUENCE: 12 atg ttc aca ggt att att gaa gaa gtc ggc aaa att gct caa att cat    48
Met Phe Thr Gly Ile Ile Glu Glu Val Gly Lys Ile Ala Gln Ile His
  1               5                  10                  15 aag caa ggc gaa ttt gcg gta gtc aca att aat gcg acc aaa gta tta    96
Lys Gln Gly Glu Phe Ala Val Val Thr Ile Asn Ala Thr Lys Val Leu
             20                  25                  30
```

```
caa gac gtt cat tta ggc gac acg att gcg gtg aac ggc gta tgt tta    144
Gln Asp Val His Leu Gly Asp Thr Ile Ala Val Asn Gly Val Cys Leu
         35                  40                  45 acc gta act tct ttt tcg agt aat cag ttt acc gcc gat gta atg tcg    192
Thr Val Thr Ser Phe Ser Ser Asn Gln Phe Thr Ala Asp Val Met Ser
 50                  55                  60 gaa acg tta aaa cgt act tca tta ggc gaa tta aag tcg aat agt ccg    240
Glu Thr Leu Lys Arg Thr Ser Leu Gly Glu Leu Lys Ser Asn Ser Pro
 65                  70                  75                  80 gtt aat tta gaa cgc gcg atg gcg gca aac gga cgt ttc ggc gga cac    288
Val Asn Leu Glu Arg Ala Met Ala Ala Asn Gly Arg Phe Gly Gly His
                 85                  90                  95 atc gtt tcg ggg cat att gac ggc acc ggc gaa att gcg gaa atc aca    336
Ile Val Ser Gly His Ile Asp Gly Thr Gly Glu Ile Ala Glu Ile Thr
            100                 105                 110 ccg gca cat aat tcg aca tgg tat cgc att aaa acc tct cca aaa tta    384
Pro Ala His Asn Ser Thr Trp Tyr Arg Ile Lys Thr Ser Pro Lys Leu
        115                 120                 125 atg cgt tat att att gag aaa ggt tcg atc acc att gac ggt att agc    432
Met Arg Tyr Ile Ile Glu Lys Gly Ser Ile Thr Ile Asp Gly Ile Ser
    130                 135                 140 ctg acc gta gtc gat acc gat gat gaa agt ttc cgt gta tcg att att    480
Leu Thr Val Val Asp Thr Asp Asp Glu Ser Phe Arg Val Ser Ile Ile
145                 150                 155                 160 ccg cat acg att aaa gaa acc aat tta ggt tcg aaa aaa atc ggc agt    528
Pro His Thr Ile Lys Glu Thr Asn Leu Gly Ser Lys Lys Ile Gly Ser
                165                 170                 175 att gtc aat tta gaa aat gat att gtc ggt aaa tat atc gaa cag ttt    576
Ile Val Asn Leu Glu Asn Asp Ile Val Gly Lys Tyr Ile Glu Gln Phe
            180                 185                 190 tta ctg aaa aag ccg gcg gat gag ccg aaa agt aat ctt agt tta gac    624
Leu Leu Lys Lys Pro Ala Asp Glu Pro Lys Ser Asn Leu Ser Leu Asp
        195                 200                 205 ttt tta aag cag gcg gga ttt                                        645
Phe Leu Lys Gln Ala Gly Phe
    210                 215

<210> SEQ ID NO 13
<211> LENGTH: 215
<212> TYPE: PRT
<213> ORGANISM: Actinobacillus pleuropneumoniae

<400> SEQUENCE: 13

Met Phe Thr Gly Ile Ile Glu Glu Val Gly Lys Ile Ala Gln Ile His
 1               5                  10                  15

Lys Gln Gly Glu Phe Ala Val Val Thr Ile Asn Ala Thr Lys Val Leu
                20                  25                  30

Gln Asp Val His Leu Gly Asp Thr Ile Ala Val Asn Gly Val Cys Leu
         35                  40                  45

Thr Val Thr Ser Phe Ser Ser Asn Gln Phe Thr Ala Asp Val Met Ser
 50                  55                  60

Glu Thr Leu Lys Arg Thr Ser Leu Gly Glu Leu Lys Ser Asn Ser Pro
 65                  70                  75                  80

Val Asn Leu Glu Arg Ala Met Ala Ala Asn Gly Arg Phe Gly Gly His
                 85                  90                  95

Ile Val Ser Gly His Ile Asp Gly Thr Gly Glu Ile Ala Glu Ile Thr
            100                 105                 110

Pro Ala His Asn Ser Thr Trp Tyr Arg Ile Lys Thr Ser Pro Lys Leu
```

```
              115                 120                 125
Met Arg Tyr Ile Ile Glu Lys Gly Ser Ile Thr Ile Asp Gly Ile Ser
    130                 135                 140

Leu Thr Val Val Asp Thr Asp Glu Ser Phe Arg Val Ser Ile Ile
145                 150                 155                 160

Pro His Thr Ile Lys Glu Thr Asn Leu Gly Ser Lys Lys Ile Gly Ser
                165                 170                 175

Ile Val Asn Leu Glu Asn Asp Ile Val Gly Lys Tyr Ile Glu Gln Phe
            180                 185                 190

Leu Leu Lys Lys Pro Ala Asp Glu Pro Lys Ser Asn Leu Ser Leu Asp
        195                 200                 205

Phe Leu Lys Gln Ala Gly Phe
    210                 215

<210> SEQ ID NO 14
<211> LENGTH: 1230
<212> TYPE: DNA
<213> ORGANISM: Actinobacillus pleuropneumoniae
<220> FEATURE:
<221> NAME/KEY: CDS
<222> LOCATION: (1)..(1230)
<223> OTHER INFORMATION: rib G

<400> SEQUENCE: 14
```

| | | | | | | | | | | | | | | | | |
|---|---|---|---|---|---|---|---|---|---|---|---|---|---|---|---|---|
| atg | aaa | tta | ccg | tgt | aag | cgg | tgg | ttt | ttc | cta | tct | ttt | tta | caa | gcc | 48 |
| Met | Lys | Leu | Pro | Cys | Lys | Arg | Trp | Phe | Phe | Leu | Ser | Phe | Leu | Gln | Ala | |
| 1 | | | | 5 | | | | | 10 | | | | | 15 | | |
| ttg | aga | tcg | aaa | gat | ttc | aag | gct | ttt | ttc | atc | att | agg | gta | aac | atg | 96 |
| Leu | Arg | Ser | Lys | Asp | Phe | Lys | Ala | Phe | Phe | Ile | Ile | Arg | Val | Asn | Met | |
| | | | 20 | | | | | 25 | | | | | 30 | | | |
| cct | gta | atg | tgt | ttt | cct | ctg | ccc | tca | aat | agt | ttc | aaa | aca | atg | acg | 144 |
| Pro | Val | Met | Cys | Phe | Pro | Leu | Pro | Ser | Asn | Ser | Phe | Lys | Thr | Met | Thr | |
| | | 35 | | | | | 40 | | | | | 45 | | | | |
| gat | tta | gac | tat | atg | cgc | cgt | gcc | att | gca | ctg | gca | aaa | caa | ggt | tta | 192 |
| Asp | Leu | Asp | Tyr | Met | Arg | Arg | Ala | Ile | Ala | Leu | Ala | Lys | Gln | Gly | Leu | |
| | 50 | | | | | 55 | | | | | 60 | | | | | |
| ggc | tgg | acg | aat | ccc | aat | ccg | ctt | gtc | ggt | tgt | gta | att | gtc | aaa | aac | 240 |
| Gly | Trp | Thr | Asn | Pro | Asn | Pro | Leu | Val | Gly | Cys | Val | Ile | Val | Lys | Asn | |
| 65 | | | | | 70 | | | | | 75 | | | | | 80 | |
| ggt | gaa | atc | gtt | gcc | gaa | ggt | tac | cat | gaa | aag | att | ggt | gga | tgg | cat | 288 |
| Gly | Glu | Ile | Val | Ala | Glu | Gly | Tyr | His | Glu | Lys | Ile | Gly | Gly | Trp | His | |
| | | | | 85 | | | | | 90 | | | | | 95 | | |
| gcg | gaa | cgt | aat | gcc | gtt | tta | cat | tgt | aag | gaa | gat | ctt | tcc | ggg | gcg | 336 |
| Ala | Glu | Arg | Asn | Ala | Val | Leu | His | Cys | Lys | Glu | Asp | Leu | Ser | Gly | Ala | |
| | | | 100 | | | | | 105 | | | | | 110 | | | |
| act | gct | tat | gta | acg | ctt | gag | cct | tgt | tgt | cat | cac | ggc | cgc | acg | ccg | 384 |
| Thr | Ala | Tyr | Val | Thr | Leu | Glu | Pro | Cys | Cys | His | His | Gly | Arg | Thr | Pro | |
| | | 115 | | | | | 120 | | | | | 125 | | | | |
| cct | tgt | tcg | gat | tta | tta | att | gaa | cga | ggc | att | aaa | aaa | gta | ttt | atc | 432 |
| Pro | Cys | Ser | Asp | Leu | Leu | Ile | Glu | Arg | Gly | Ile | Lys | Lys | Val | Phe | Ile | |
| | 130 | | | | | 135 | | | | | 140 | | | | | |
| ggt | tcg | agc | gat | ccg | aat | cct | tta | gta | gca | ggg | cgg | gga | gca | aat | cag | 480 |
| Gly | Ser | Ser | Asp | Pro | Asn | Pro | Leu | Val | Ala | Gly | Arg | Gly | Ala | Asn | Gln | |
| 145 | | | | | 150 | | | | | 155 | | | | | 160 | |
| cta | cgc | caa | gcc | ggc | gtg | gaa | gtg | gtg | gaa | ggt | tta | ctc | aaa | gaa | gaa | 528 |
| Leu | Arg | Gln | Ala | Gly | Val | Glu | Val | Val | Glu | Gly | Leu | Leu | Lys | Glu | Glu | |
| | | | | 165 | | | | | 170 | | | | | 175 | | |
| tgt | gat | gcg | tta | aac | ccg | att | ttt | ttc | cac | tat | att | caa | act | aaa | cgt | 576 |
| Cys | Asp | Ala | Leu | Asn | Pro | Ile | Phe | Phe | His | Tyr | Ile | Gln | Thr | Lys | Arg | |
| | | | 180 | | | | | 185 | | | | | 190 | | | |

```
ccg tat gtg cta atg aaa tat gcc atg acg gca gac ggc aaa att gca      624
Pro Tyr Val Leu Met Lys Tyr Ala Met Thr Ala Asp Gly Lys Ile Ala
            195                 200                 205 acc ggt agc ggc gaa tcc aaa tgg att acc ggt gaa tcg gca aga gca      672
Thr Gly Ser Gly Glu Ser Lys Trp Ile Thr Gly Glu Ser Ala Arg Ala
210                 215                 220 aga gtg cag caa aca cgt cat caa tat agt gcg att atg gtc ggt gta      720
Arg Val Gln Gln Thr Arg His Gln Tyr Ser Ala Ile Met Val Gly Val
225                 230                 235                 240 gat acg gta ctt gcc gat aac ccg atg tta aat agc cga atg ccg aat      768
Asp Thr Val Leu Ala Asp Asn Pro Met Leu Asn Ser Arg Met Pro Asn
            245                 250                 255 gcg aaa caa ccg gtc cgg att gtc tgc gat agc caa tta cgt aca ccg      816
Ala Lys Gln Pro Val Arg Ile Val Cys Asp Ser Gln Leu Arg Thr Pro
                260                 265                 270 tta gat tgc cag tta gtg cag aca gcg aaa gaa tat cgc acc gta att      864
Leu Asp Cys Gln Leu Val Gln Thr Ala Lys Glu Tyr Arg Thr Val Ile
                275                 280                 285 gca acc gtt agt gac gat ttg caa aaa att gaa caa ttt aga ccg ctt      912
Ala Thr Val Ser Asp Asp Leu Gln Lys Ile Glu Gln Phe Arg Pro Leu
290                 295                 300 ggc gta gat gta tta gtg tgt aaa gca cga aac aag cgg gta gat ttg      960
Gly Val Asp Val Leu Val Cys Lys Ala Arg Asn Lys Arg Val Asp Leu
305                 310                 315                 320 caa gat ctt ttg caa aag ctc ggt gaa atg cag atc gac agc ctc tta     1008
Gln Asp Leu Leu Gln Lys Leu Gly Glu Met Gln Ile Asp Ser Leu Leu
            325                 330                 335 ttg gaa ggc ggt tca agt ttg aat ttc agt gcg tta gaa agc ggt atc     1056
Leu Glu Gly Gly Ser Ser Leu Asn Phe Ser Ala Leu Glu Ser Gly Ile
                340                 345                 350 gtg aat cga gta cat tgt tat att gcg cct aaa tta gtc ggt ggt aaa     1104
Val Asn Arg Val His Cys Tyr Ile Ala Pro Lys Leu Val Gly Gly Lys
                355                 360                 365 caa gcg aaa acc cca atc ggc ggt gag gga att caa caa atc gac caa     1152
Gln Ala Lys Thr Pro Ile Gly Gly Glu Gly Ile Gln Gln Ile Asp Gln
370                 375                 380 gcg gtt aaa tta aaa ttg aaa tcg acc gaa ctc atc ggc gaa gat att     1200
Ala Val Lys Leu Lys Leu Lys Ser Thr Glu Leu Ile Gly Glu Asp Ile
385                 390                 395                 400 ttg ttg gat tat gta gtc atc tcc cct ctt                             1230
Leu Leu Asp Tyr Val Val Ile Ser Pro Leu
            405                 410

<210> SEQ ID NO 15
<211> LENGTH: 410
<212> TYPE: PRT
<213> ORGANISM: Actinobacillus pleuropneumoniae

<400> SEQUENCE: 15

Met Lys Leu Pro Cys Lys Arg Trp Phe Phe Leu Ser Phe Leu Gln Ala
1               5                   10                  15

Leu Arg Ser Lys Asp Phe Lys Ala Phe Ile Ile Arg Val Asn Met
            20                  25                  30

Pro Val Met Cys Phe Pro Leu Pro Ser Asn Ser Phe Lys Thr Met Thr
            35                  40                  45

Asp Leu Asp Tyr Met Arg Arg Ala Ile Ala Leu Ala Lys Gln Gly Leu
        50                  55                  60

Gly Trp Thr Asn Pro Asn Pro Leu Val Gly Cys Val Ile Val Lys Asn
65                  70                  75                  80
```

```
Gly Glu Ile Val Ala Glu Gly Tyr His Glu Lys Ile Gly Gly Trp His
                85                  90                  95

Ala Glu Arg Asn Ala Val Leu His Cys Lys Glu Asp Leu Ser Gly Ala
            100                 105                 110

Thr Ala Tyr Val Thr Leu Glu Pro Cys Cys His His Gly Arg Thr Pro
        115                 120                 125

Pro Cys Ser Asp Leu Leu Ile Glu Arg Gly Ile Lys Lys Val Phe Ile
    130                 135                 140

Gly Ser Ser Asp Pro Asn Pro Leu Val Ala Gly Arg Gly Ala Asn Gln
145                 150                 155                 160

Leu Arg Gln Ala Gly Val Glu Val Val Glu Gly Leu Leu Lys Glu Glu
                165                 170                 175

Cys Asp Ala Leu Asn Pro Ile Phe Phe His Tyr Ile Gln Thr Lys Arg
            180                 185                 190

Pro Tyr Val Leu Met Lys Tyr Ala Met Thr Ala Asp Gly Lys Ile Ala
        195                 200                 205

Thr Gly Ser Gly Glu Ser Lys Trp Ile Thr Gly Glu Ser Ala Arg Ala
    210                 215                 220

Arg Val Gln Gln Thr Arg His Gln Tyr Ser Ala Ile Met Val Gly Val
225                 230                 235                 240

Asp Thr Val Leu Ala Asp Asn Pro Met Leu Asn Ser Arg Met Pro Asn
                245                 250                 255

Ala Lys Gln Pro Val Arg Ile Val Cys Asp Ser Gln Leu Arg Thr Pro
            260                 265                 270

Leu Asp Cys Gln Leu Val Gln Thr Ala Lys Glu Tyr Arg Thr Val Ile
        275                 280                 285

Ala Thr Val Ser Asp Asp Leu Gln Lys Ile Glu Gln Phe Arg Pro Leu
    290                 295                 300

Gly Val Asp Val Leu Val Cys Lys Ala Arg Asn Lys Arg Val Asp Leu
305                 310                 315                 320

Gln Asp Leu Leu Gln Lys Leu Gly Glu Met Gln Ile Asp Ser Leu Leu
                325                 330                 335

Leu Glu Gly Gly Ser Ser Leu Asn Phe Ser Ala Leu Glu Ser Gly Ile
            340                 345                 350

Val Asn Arg Val His Cys Tyr Ile Ala Pro Lys Leu Val Gly Gly Lys
        355                 360                 365

Gln Ala Lys Thr Pro Ile Gly Gly Glu Gly Ile Gln Gln Ile Asp Gln
    370                 375                 380

Ala Val Lys Leu Lys Leu Lys Ser Thr Glu Leu Ile Gly Glu Asp Ile
385                 390                 395                 400

Leu Leu Asp Tyr Val Val Ile Ser Pro Leu
                405                 410

<210> SEQ ID NO 16
<211> LENGTH: 459
<212> TYPE: DNA
<213> ORGANISM: Actinobacillus pleuropneumoniae
<220> FEATURE:
<221> NAME/KEY: CDS
<222> LOCATION: (1)..(459)
<223> OTHER INFORMATION: rib H

<400> SEQUENCE: 16 atg gca aag att aca ggt aac tta gtt gcg aca ggt tta aaa ttc ggt      48
Met Ala Lys Ile Thr Gly Asn Leu Val Ala Thr Gly Leu Lys Phe Gly
  1               5                  10                  15
```

```
att gta acc gca cgt ttc aac gat ttt atc aac gat aaa tta tta agc      96
Ile Val Thr Ala Arg Phe Asn Asp Phe Ile Asn Asp Lys Leu Leu Ser
         20                  25                  30 ggt gca att gat acg tta gtg cgt cac ggt gcg tat gaa aac gat att     144
Gly Ala Ile Asp Thr Leu Val Arg His Gly Ala Tyr Glu Asn Asp Ile
             35                  40                  45 gat acg gca tgg gtt ccg ggt gca ttt gag att cca tta gtt gcg aaa     192
Asp Thr Ala Trp Val Pro Gly Ala Phe Glu Ile Pro Leu Val Ala Lys
 50                  55                  60 aaa atg gca aac agc ggt aaa tat gat gcg gta atc tgt tta ggt acg     240
Lys Met Ala Asn Ser Gly Lys Tyr Asp Ala Val Ile Cys Leu Gly Thr
 65                  70                  75                  80 gta att cgc ggt tcg aca act cac tat gat tac gta tgt aat gaa gcg     288
Val Ile Arg Gly Ser Thr Thr His Tyr Asp Tyr Val Cys Asn Glu Ala
                 85                  90                  95 gca aaa ggt atc ggt gcg gta gca tta gaa acc ggc gta ccg gta att     336
Ala Lys Gly Ile Gly Ala Val Ala Leu Glu Thr Gly Val Pro Val Ile
            100                 105                 110 ttc ggt gta tta acc aca gaa aat att gaa cag gcg att gaa cgc gcg     384
Phe Gly Val Leu Thr Thr Glu Asn Ile Glu Gln Ala Ile Glu Arg Ala
        115                 120                 125 ggt act aaa gca ggt aat aaa ggt tca gaa tgt gca tta ggc gca atc     432
Gly Thr Lys Ala Gly Asn Lys Gly Ser Glu Cys Ala Leu Gly Ala Ile
    130                 135                 140 gaa ata gta aac gta tta aaa gcg atc                                 459
Glu Ile Val Asn Val Leu Lys Ala Ile
145                 150

<210> SEQ ID NO 17
<211> LENGTH: 153
<212> TYPE: PRT
<213> ORGANISM: Actinobacillus pleuropneumoniae

<400> SEQUENCE: 17

Met Ala Lys Ile Thr Gly Asn Leu Val Ala Thr Gly Leu Lys Phe Gly
  1               5                  10                  15

Ile Val Thr Ala Arg Phe Asn Asp Phe Ile Asn Asp Lys Leu Leu Ser
             20                  25                  30

Gly Ala Ile Asp Thr Leu Val Arg His Gly Ala Tyr Glu Asn Asp Ile
         35                  40                  45

Asp Thr Ala Trp Val Pro Gly Ala Phe Glu Ile Pro Leu Val Ala Lys
 50                  55                  60

Lys Met Ala Asn Ser Gly Lys Tyr Asp Ala Val Ile Cys Leu Gly Thr
 65                  70                  75                  80

Val Ile Arg Gly Ser Thr Thr His Tyr Asp Tyr Val Cys Asn Glu Ala
                 85                  90                  95

Ala Lys Gly Ile Gly Ala Val Ala Leu Glu Thr Gly Val Pro Val Ile
            100                 105                 110

Phe Gly Val Leu Thr Thr Glu Asn Ile Glu Gln Ala Ile Glu Arg Ala
        115                 120                 125

Gly Thr Lys Ala Gly Asn Lys Gly Ser Glu Cys Ala Leu Gly Ala Ile
    130                 135                 140

Glu Ile Val Asn Val Leu Lys Ala Ile
145                 150
```